US011730460B2

(12) United States Patent
Maeda et al.

(10) Patent No.: US 11,730,460 B2
(45) Date of Patent: Aug. 22, 2023

(54) THERAPEUTIC SUBSTANCE DELIVERY DEVICE AND THERAPEUTIC SUBSTANCE DELIVERY KIT

(71) Applicant: TOKYO WOMEN'S MEDICAL UNIVERSITY, Tokyo (JP)

(72) Inventors: Masanori Maeda, Tokyo (JP); Nobuo Kanai, Tokyo (JP); Yusuke Fujii, Tokyo (JP); Masayuki Yamato, Tokyo (JP); Makoto Abe, Tokyo (JP)

(73) Assignee: TOKYO WOMEN'S MEDICAL UNIVERSITY, Tokyo (JP)

( * ) Notice: Subject to any disclaimer, the term of this patent is extended or adjusted under 35 U.S.C. 154(b) by 972 days.

(21) Appl. No.: 15/757,765

(22) PCT Filed: Sep. 8, 2016

(86) PCT No.: PCT/JP2016/076511
§ 371 (c)(1),
(2) Date: Mar. 6, 2018

(87) PCT Pub. No.: WO2017/043600
PCT Pub. Date: Mar. 16, 2017

(65) Prior Publication Data
US 2020/0352550 A1    Nov. 12, 2020

(30) Foreign Application Priority Data

Sep. 9, 2015   (JP) .................................. 2015-177993

(51) Int. Cl.
*A61B 17/00* (2006.01)

(52) U.S. Cl.
CPC .................. *A61B 17/00234* (2013.01); *A61B 2017/00296* (2013.01); *A61B 2017/00305* (2013.01);
(Continued)

(58) Field of Classification Search
CPC .... A61B 17/00234; A61B 2017/00296; A61B 2017/00305; A61B 2017/00969;
(Continued)

(56) References Cited

U.S. PATENT DOCUMENTS 8,926,576 B2   1/2015   Mikkaichi
9,078,662 B2 *  7/2015   Bakos ..................... H02J 50/10
(Continued)

FOREIGN PATENT DOCUMENTS

CN         2912817 Y  *  6/2007
CN       204016241 U  * 12/2014  ......... A61B 1/00128
(Continued)

OTHER PUBLICATIONS

International Application No. PCT/JP2016/076511, International Search Report dated Oct. 11, 2016, 1 page.

*Primary Examiner* — Lynsey C Eiseman
*Assistant Examiner* — Ranjani Mari Sundaresan
(74) *Attorney, Agent, or Firm* — Kilpatrick Townsend & Stockton LLP

(57) ABSTRACT

The present invention relates to a therapeutic substance delivery device for delivering a therapeutic substance to a desired site in a bodily duct, characterized in that the therapeutic substance delivery device is provided with: a therapeutic substance loading portion; a connector which is connected to the therapeutic substance loading portion; and a supplying/discharging pipe connected to the connector; and in that the therapeutic substance loading portion includes a main body portion in which a recessed portion is formed, a resilient film, and a connecting pipe; the connector is provided with a joint main body, a flange portion fixed to the other end portion side of the joint main body, and a fixing nut through which the joint main body passes; the joint main body is provided with a tube fastening portion; and at least part of the inner wall of the fixing nut is provided with a thread.

18 Claims, 17 Drawing Sheets

(52) U.S. Cl.
CPC .......... *A61B 2017/00969* (2013.01); *A61B 2217/005* (2013.01); *A61B 2217/007* (2013.01)

(58) Field of Classification Search
CPC ........ A61B 2217/005; A61B 2217/007; A61B 2017/00292; A61M 37/0069; A61M 2025/105; A61M 2025/1054; A61M 2025/1077; A61M 25/1002; A61M 25/10184; A61M 29/02; A61M 2025/0079; A61M 2025/0096; A61F 2/958; A61K 9/0024; A61K 9/0092
See application file for complete search history.

(56) References Cited

U.S. PATENT DOCUMENTS

| | | | |
|---|---|---|---|
| 2011/0004057 A1* | 1/2011 | Goldfarb | A61M 29/02 600/106 |
| 2014/0150782 A1* | 6/2014 | Vazales | A61B 1/126 128/202.16 |
| 2016/0331645 A1* | 11/2016 | Bagwell | A61B 17/3207 |

FOREIGN PATENT DOCUMENTS

| | | | | |
|---|---|---|---|---|
| JP | H07100065 B1 * | 11/1995 | | |
| JP | H07100065 B2 * | 11/1995 | .......... | A61M 1/0086 |
| JP | 2008-148887 A | 7/2008 | | |
| JP | 2009-213900 A | 9/2009 | | |
| JP | 2010-504808 A | 2/2010 | | |
| JP | 5450904 B2 | 3/2014 | | |
| WO | WO-9417856 A1 * | 8/1994 | .............. | A61N 1/40 |
| WO | 2008/039249 A1 | 4/2008 | | |
| WO | WO-2015095214 A1 * | 6/2015 | ......... | A61B 1/00124 |

\* cited by examiner

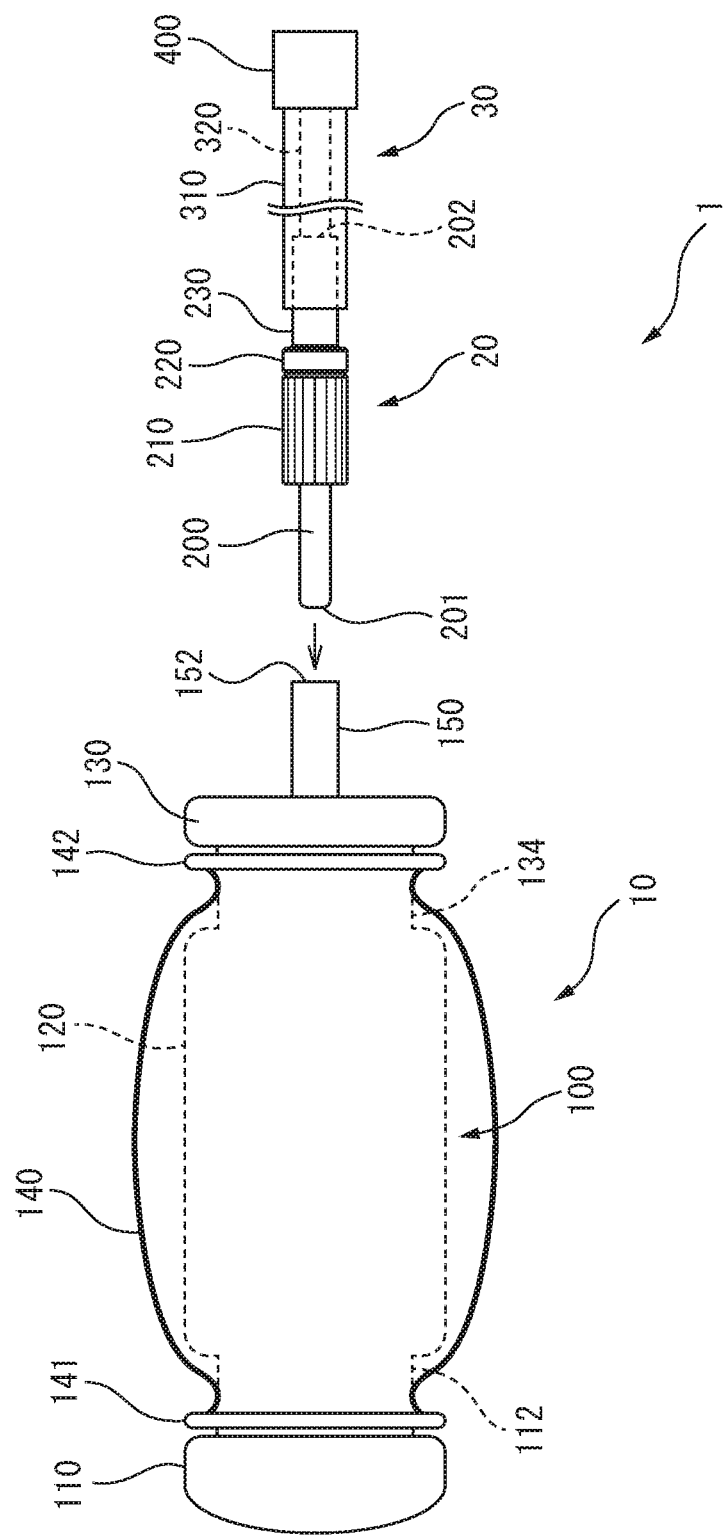

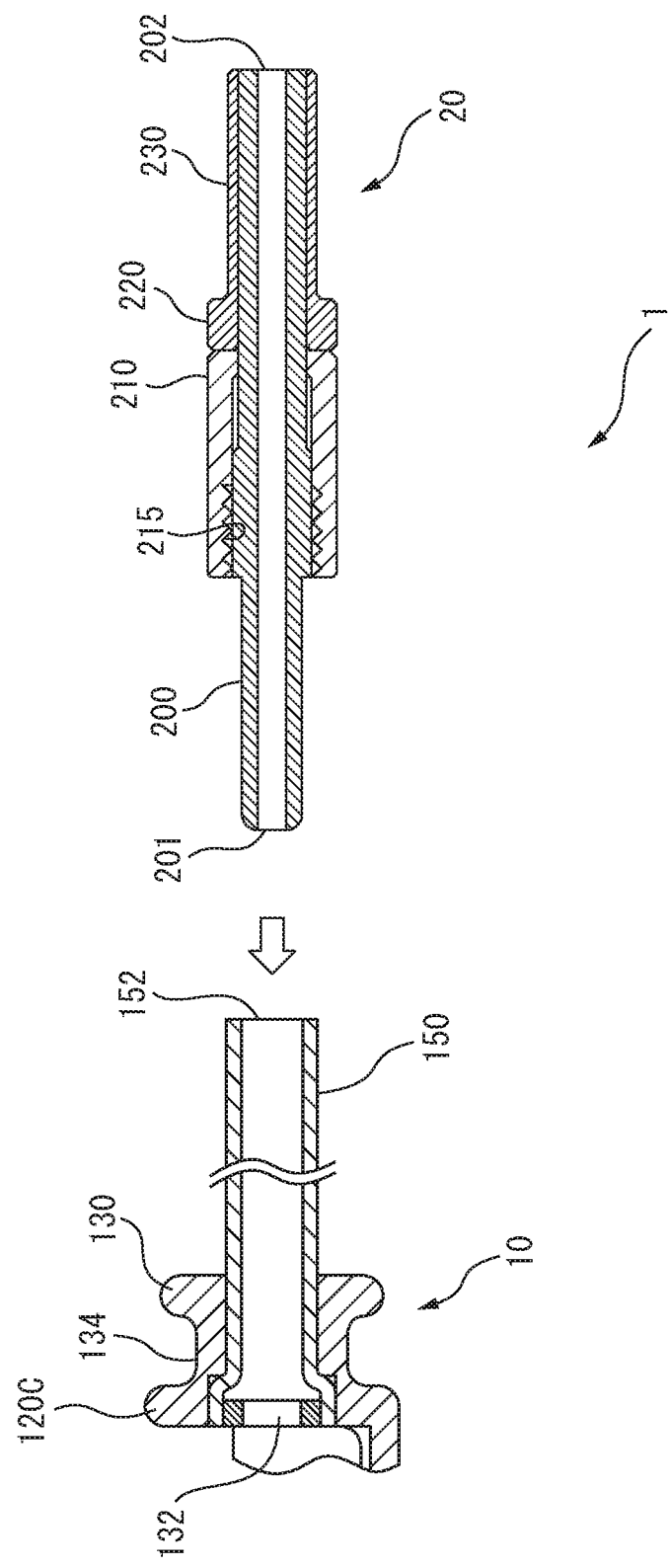

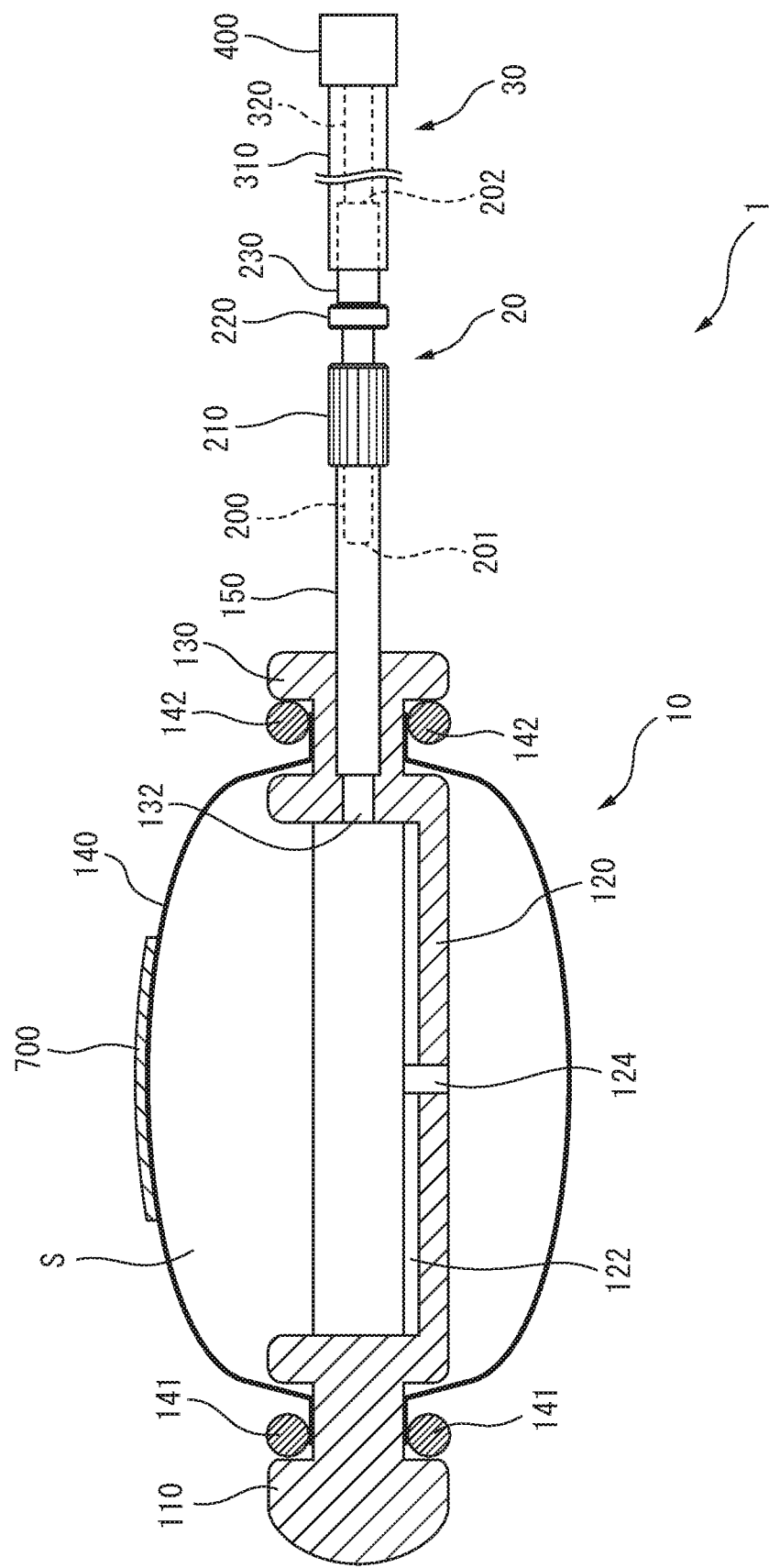

THERAPEUTIC SUBSTANCE DELIVERY DEVICE AND THERAPEUTIC SUBSTANCE DELIVERY KIT

CROSS-REFERENCE TO RELATED APPLICATIONS

This application is a 371 National Phase application of PCT/JP2016/076511, filed Sep. 8, 2016, which application claims priority to Japanese Application No. 2015-177993, filed Sep. 9, 2015, the teachings both of which are hereby incorporated by reference in their entireties for all purposes.

TECHNICAL FIELD

The present invention relates to a therapeutic substance conveying device. The invention further relates to a therapeutic substance conveying kit.

BACKGROUND ART

Recent remarkable developments in the field of regenerative medicine are leading to attempts to find methods of regenerating various diseased organs and tissues. Attempts are being made to promote regeneration of diseased or damaged organs or tissues by applying therapeutic substances to the organs or tissues. One technique in regenerative medicine that is being developed is a technique in which a culture dish coated with a temperature-responsive polymer is used for culturing of cells as a sheet after which the cells are collected, and treatment methods in which these are applied to affected parts are being developed (PTLs 1 to 3). This technique allows transplanting of the cells themselves in the form of a sheet, and it has constituted a major leap forward in regenerative medicine.

Cell sheets are used as a method of treatment to prevent esophageal stenosis caused after Endoscopic Submucosal Dissection (ESD) in which early-stage esophageal cancer is excised. When ESD is carried out in cases where lesions are found over a wide area of the esophagus, ulcers form over a wide region at the site of lesion excision, causing stenosis. For patients in which stenosis has occurred, the conventionally employ method of treatment has been to insert a balloon at the site of stenosis to physically spread it open. This method of treatment, however, produces intense pain when the site of stenosis is spread open, the treatment being carried out usually 20 to 30 times or even up to 50 times in some cases, and this has been an issue as it forces a huge burden to be borne by patients. In order to solve this problem, a method of treatment has been developed in which a tissue sample is harvested from the patient's own oral mucosa, and a temperature-responsive culture dish is used to prepare an oral mucosa epithelial cell sheet, which is transplanted onto the esophageal ulcer surface under endoscopic observation following ESD. This has made it possible to prevent post-ESD esophageal stenosis and significantly contribute to alleviating the burden on patients (NPL 1).

A cell sheet is composed of a very thin membrane of one or more cell layers, and it is extremely difficult to manage. In order to obtain a therapeutic effect by a cell sheet, a level of technical skill is necessary for reliably conveying the cell sheet to the desired site of application and properly applying it. However, in order for treatment techniques using cell sheets to become more commonplace there is a need for devices that allow cell sheets to be conveniently and reproducibly applied to desired sites even by practitioners with an ordinary level of skill, and the development of such devices has been desired. The difficulty increases particularly when the affected part is a biological canal such as the esophagus or intestinal tract, as it is necessary to apply the cell sheet on the inner luminal side. Conveying jigs (conveying tools) have been developed to deal with this problem. For example, PTL 4 discloses a biological tract interior treatment device comprising a tubular section, a balloon provided in an inflatable manner on the outer circumference of the tubular section, and inflation means that causes the balloon to inflate, the balloon being inserted in a biological tract with the balloon in the contracted state, and the balloon being caused to expand by the inflation means, coming into pressure contact with the inner wall of the biological tract and causing the cell sheet to indwell in the biological tract (see PTL 4).

CITATION LIST

Patent Literature

[PTL 1] Japanese Unexamined Patent Publication HEI No. 02-211865
[PTL 2] Japanese Unexamined Patent Publication HEI No. 05-192138
[PTL 3] Domestic Re-publication of PCT International Application 02-008387
[PTL 4] Japanese Unexamined Patent Publication No. 2008-148887

Non-Patent Literature

[NPL 1] Ohki T, Yamato M, Murakami D, Takagi R, Yang J, Namiki H, et al. Treatment of oesophageal ulcerations using endoscopic transplantation of tissue-engineered autologous oral mucosal epithelial cell sheets in a canine model. Gut. 2006; 55(12):1704-10.

SUMMARY OF INVENTION

Technical Problem

However, the biological tract interior treatment device (treatment device) disclosed in PTL 4 is a device used separately from the endoscope, and in order to accurately allow the treatment device to reach the affected part and apply the therapeutic substance it has been necessary to learn how to operate both the device and the endoscope. Even when using a mode in which an airflow tube is inserted through the forceps channel of the endoscope, and the treatment device is connected to the airflow tube that has left the exit of the forceps channel by pressure fitting so that it is integral with the endoscope, the device and the airflow tube are only weakly connected, and when catching on irregularities in the biological tract they can potentially fall off into the biological tract.

Moreover, the treatment device is a device having the therapeutic substance carried while the balloon is in close contact with the peripheral surface of the tubular section by contraction, and it is inserted into the biological tract through a sheath situated in the biological tract, the treatment device protruding from the tip section of the sheath to reach the affected part. A biological tract is curved and highly irregular, and consequently when the treatment device protrudes out from the sheath, the tip of the treatment device presses against the inner wall of the biological tract, changing its position from the state before it protruded, and potentially resulting in the tip of the sheath or the inner wall of the biological tract contacting with the therapeutic substance. Particularly when the therapeutic substance is a cell sheet, the cell sheet being a thin, soft substance, its contact with the sheath tip or biological tract may result in its crimping or twisting, which is an undesirable state that is unsuitable for application to affected parts.

It is an object of the present invention to provide a therapeutic substance conveying device that prevents contact of the therapeutic substance with other objects in a biological tract, while preventing the therapeutic substance-carrying unit from falling off into the biological tract, and wherein the therapeutic substance-carrying unit is detachable from an air supply/discharge tube.

Solution to Problem

The disclosed technique employs the following means for solving the problems described above.

Specifically, the first aspect of the invention is:

A therapeutic substance conveying device for conveying and/or applying a therapeutic substance to a desired site in a biological tract, comprising:

a therapeutic substance-carrying unit, a connector connected to the therapeutic substance-carrying unit, and an air supply/discharge tube connected to the connector, wherein the therapeutic substance-carrying unit has a body portion in which a recess is formed, an elastic membrane covering at least the recess and forming an inner space with the body portion, and a connecting tube of which at least one end is made of a flexible material, and which communicates with the inner space, the connector comprises a coupling body with a through-hole through which fluid passes and having one end for insertion into the connecting tube and the other end connected to the air supply/discharge tube, a flange section anchored to the other end of the coupling body and an anchoring nut through which the coupling body is inserted, the coupling body comprises a tube catch section having a larger diameter than the outer diameter of the coupling body and a smaller diameter than the inner diameter of the anchoring nut, and at least a portion of the inner wall of the anchoring nut is provided with an internal thread, forward screwing of the anchoring nut causes the internal thread to bite into the connecting tube sandwiched between the anchoring nut and the coupling body, and the therapeutic substance-carrying unit is detachable.

According to the first aspect it is possible to provide a therapeutic substance conveying device that prevents the therapeutic substance-carrying unit on which the therapeutic substance is carried from falling off into the biological tract, and can prevent the therapeutic substance carried on the therapeutic substance-carrying unit from coming into contact with other substances.

The second aspect of the invention is a therapeutic substance conveying device according to first aspect, wherein the air supply/discharge tube is inserted through the forceps channel of an endoscope and is used together with the endoscope.

According to the second aspect, it is possible to use the therapeutic substance conveying device through the forceps channel of the endoscope.

The third aspect of the invention is a therapeutic substance conveying device according to the first or second aspect, wherein the anchoring nut comprises a tubular screw part and a collar section having an insertion hole through which the coupling body is inserted, and the diameter of the insertion hole is a smaller diameter than the outer diameter of the tube catch section.

According to the third aspect, not only is it possible to prevent the anchoring nut of the therapeutic substance conveying device of the invention from falling off from one end of the coupling body, but the contact surface between the anchoring nut and the tube catch section also functions as a fulcrum during forward screwing of the anchoring nut to anchor the connecting tube, and the force of pressure contact of the connecting tube on the tube catch section is concentrated for a more firm connection.

The fourth mode of the invention is a therapeutic substance conveying device according to the third aspect, wherein the outer diameter of the flange section is a smaller diameter than the outer diameter of the anchoring nut and a larger diameter than the diameter of the insertion hole of the collar section.

According to the fourth aspect, it is possible to prevent the anchoring nut of the therapeutic substance conveying device of the invention from falling off from the other end of the coupling body.

The fifth aspect of the invention is a therapeutic substance conveying device according to the first to fourth aspects, wherein the outer diameter of the connector is less than 5.0 mm.

According to the fifth aspect, it is possible to provide a therapeutic substance conveying device capable of passing through the forceps channel of an endoscope.

The sixth aspect of the invention is a therapeutic substance conveying device according to the first to fifth aspects, wherein the tube catch section is formed in a tapered manner with increasing diameter from one end of the coupling body toward the other end.

According to the sixth aspect, the connecting tube of the therapeutic substance-carrying unit is inserted while spreading out along the tapered form of the tube catch section, so that leakage of fluids from between the connector and the connecting tube can be prevented.

The seventh aspect of the invention is a therapeutic substance conveying device according to the first to sixth aspects, wherein inflation means for causing inflow and discharge of fluid in the inner space of the therapeutic substance-carrying unit is also connected to the air supply/discharge tube.

According to the seventh aspect it is possible to inflate the elastic membrane of the therapeutic substance-carrying unit by inflation means, allowing the therapeutic substance to be conveyed while being carried by the recessed therapeutic substance-carrying unit, and helping to prevent the therapeutic substance from falling off by the inner wall inside the biological tract. In addition, by causing the elastic membrane to expand, it is possible to apply the therapeutic substance by pressing it against the affected part inside the biological tract.

The eighth aspect of the invention is a therapeutic substance conveying device according to the first to seventh aspects, wherein the therapeutic substance-carrying unit is for single-use.

According to the eighth aspect, the therapeutic substance-carrying unit can be exchanged with a sterilized therapeutic substance-carrying unit, and sterilized therapeutic substance-carrying units may be continuously prepared and utilized depending on the number of therapeutic substances required and their amounts.

The ninth aspect of the invention is a therapeutic substance conveying device according to the first to eighth aspects, wherein the body portion of the therapeutic substance-carrying unit is an approximately half-elliptical tube shape with a portion of the peripheral surface removed.

According to the ninth aspect, when the therapeutic substance conveying device of the invention has been used through the forceps channel of an endoscope, it is easier to see both the elastic membrane portion of the endoscope on which the therapeutic substance is carried and the affected part, through the tip of the endoscope, thereby allowing the therapeutic substance to be reliably applied.

The tenth aspect of the invention is a therapeutic substance conveying device according to the first to ninth aspects, wherein the therapeutic substance-carrying unit comprises a body portion having at least a recess-formed middle section between one end and the other end, and the elastic membrane is formed as a tube with two ends, the one end and the other end of the elastic membrane being in close contact with and anchored to the middle section, while being wrapped around the perimeter of the middle section.

According to the tenth aspect, the elastic membrane wrapped around the body portion of the therapeutic substance-carrying unit expands in the form a barrel, and presses across the entire periphery of the inside of the biological tract, allowing the therapeutic substance to be anchored and applied.

The eleventh aspect of the invention is a therapeutic substance conveying device according to the first to eighth aspects, wherein the body portion of the therapeutic substance-carrying unit has an approximately half-spheroid shape or approximately half-egg shape in which a recess has been formed, and the elastic membrane is in close contact and anchored with the edge of the body portion.

According to the eleventh aspect, it is possible to expand only an elastic membrane covering half of the surface of the therapeutic substance-carrying unit, and therefore the entire periphery of the inside of the biological tract is not blocked and the therapeutic substance can be anchored and applied while ensuring visibility through the endoscope.

The twelfth aspect of the invention is a therapeutic substance conveying device according to the first to tenth aspects, wherein the body portion has black or dark coloration.

According to the twelfth aspect, the body portion of the therapeutic substance-carrying unit is black or dark colored, and therefore the proportion of reflection of light from the phosphor at the tip section of the endoscope is reduced, and the visibility of the therapeutic substance carried on the therapeutic substance-carrying unit is increased.

The thirteenth aspect of the invention is a therapeutic substance conveying kit for conveying and/or applying a therapeutic substance to a desired site in a biological tract, comprising:

a therapeutic substance-carrying unit, a connector to be connected to the therapeutic substance-carrying unit, and an air supply/discharge tube to be connected to the connector, wherein the therapeutic substance-carrying unit has a body portion in which a recess is formed, an elastic membrane covering at least the recess and forming an inner space with the body portion, and a connecting tube of which at least one end is made of a flexible material, and which communicates with the inner space, the connector comprises a coupling body with a through-hole through which fluid passes and having one end for insertion into the connecting tube and the other end connected to the air supply/discharge tube, a flange section anchored to the other end of the coupling body and an anchoring nut through which the coupling body is inserted, the coupling body comprises a tube catch section having a larger diameter than the outer diameter of the coupling body and a smaller diameter than the inner diameter of the anchoring nut, and at least a portion of the inner wall of the anchoring nut is provided with an internal thread, forward screwing of the anchoring nut causes the internal thread to bite into the connecting tube sandwiched between the anchoring nut and the coupling body, and the therapeutic substance-carrying unit is detachable.

According to the thirteenth aspect there is provided a kit including a therapeutic substance-carrying unit, a connector and an air supply/discharge tube, such that, even when the therapeutic substance-carrying unit, connector and air supply/discharge tube are separately provided, for example, it is possible to provide a therapeutic substance conveying device of the invention by combining them.

The fourteenth aspect of the invention is a therapeutic substance conveying kit according to the thirteenth aspect, wherein inflation means for causing inflow and discharge of fluid in the inner space of the therapeutic substance-carrying unit, connected with the air supply/discharge tube, is additionally provided.

According to the fourteenth aspect, means for inflating the elastic membrane of the therapeutic substance-carrying unit is additionally provided, and their combination allows a therapeutic substance conveying device of the invention to be provided.

The fifteenth aspect of the invention is a therapeutic substance conveying kit according to the thirteenth or fourteenth aspect, wherein a therapeutic substance is further carried on the therapeutic substance-carrying unit.

According to the fifteenth aspect, it is possible to provide a therapeutic substance conveying kit having a therapeutic substance carried on the therapeutic substance-carrying unit beforehand.

Advantageous Effects of Invention

With the technology disclosed by the present invention, it is possible to provide a therapeutic substance conveying device that prevents contact of the therapeutic substance with other objects in a biological tract, while preventing the therapeutic substance-carrying unit from falling off into the biological tract, and wherein the therapeutic substance-carrying unit is detachable from the air supply/discharge tube.

BRIEF DESCRIPTION OF DRAWINGS

FIG. 1 is a diagram showing an example of the construction of a therapeutic substance conveying device according to an embodiment.

FIG. 2A is a cross-sectional view showing the connector and therapeutic substance-carrying unit of the embodiment.

FIG. 5B is a diagram showing an example of the construction of a therapeutic substance conveying device according to the embodiment.

DESCRIPTION OF EMBODIMENTS

Figure 2B:
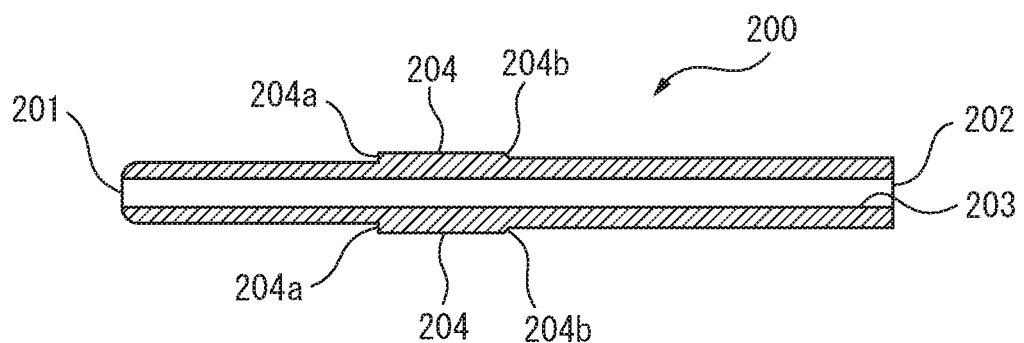
FIG. 2B is a cross-sectional view showing the coupling body of the connector of the embodiment.
Figure 2C:
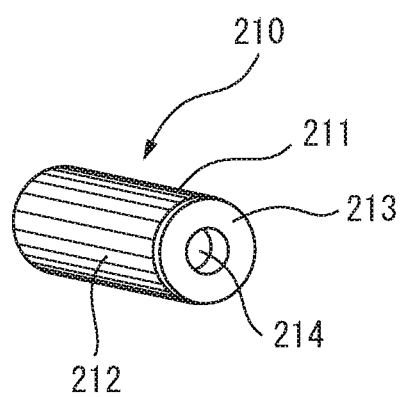
FIG. 2C is a perspective view showing the anchoring nut of the connector of the embodiment.
Figure 2D:
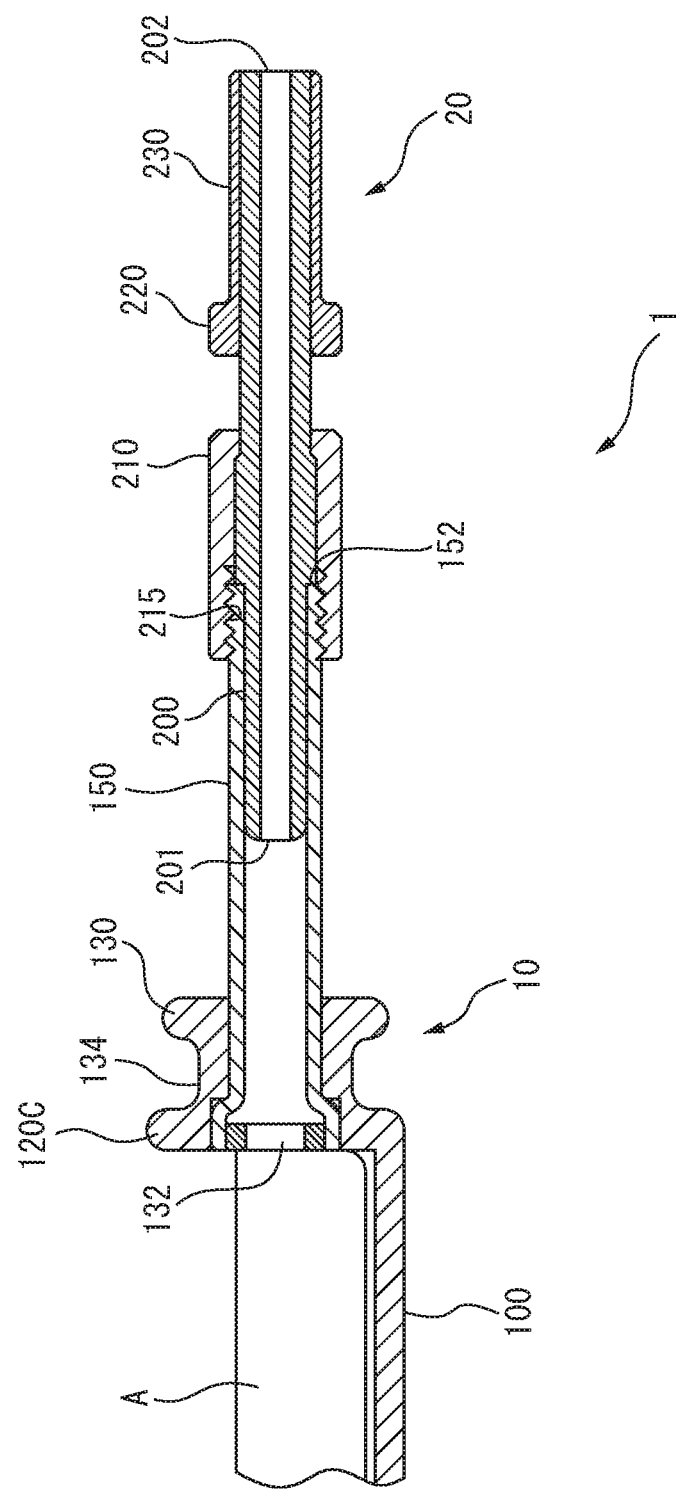
FIG. 2D is a cross-sectional view showing the connector and therapeutic substance-carrying unit of the embodiment.

An embodiment of the present invention will now be described with reference to the accompanying drawings. The construction of this embodiment is merely an example and the construction of the invention is not limited by the concrete construction of the embodiment.

Embodiment

<Construction Example of Therapeutic Substance Conveying Jig>

FIG. 1 is a diagram showing an example of the construction of a device for conveying a therapeutic substance according to this embodiment (hereunder also referred to simply as "therapeutic substance conveying device 1"). The therapeutic substance conveying device 1 comprises a therapeutic substance-carrying unit 10 for carrying of a therapeutic substance, an air supply/discharge tube 30 for supply and discharge of a fluid through the therapeutic substance-carrying unit 10, and a connecting tube connector that connects the therapeutic substance-carrying unit 10 and the air supply/discharge tube 30 (hereunder also referred to as "connector 20").

The therapeutic substance-carrying unit 10 comprises a body portion 100 with one end 110, a middle section 120 and another end 130 in the lengthwise direction, and a balloon 140 (an example of an "elastic membrane") that covers the body portion 100 in a manner wrapped around the perimeter of the middle section 120. A connecting tube 150 is bonded at the end face of the other end 130 of the body portion 100 of the therapeutic substance-carrying unit 10. The therapeutic substance-carrying unit 10 can be freely detached from the air supply/discharge tube 30 that is used for air supply and discharge to and from the inner space formed by the body portion 100 and the balloon 140, as well as for application of rotary force (torque) in the circumferential direction of the body portion 100, via the connector 20.

A female luer connector (not shown) is also bonded to the other end of the air supply/discharge tube 30. The luer connector is connected to a male connector of inflation means 400 that carries out air supply and discharge to and from the inner space and inflates the balloon 140. The inflation means 400 is a syringe or a pump, for example. The luer connector may also be a connector having the same construction as the connector 20.

1. Therapeutic Substance Conveying Device

Each of the constituent elements of the therapeutic substance conveying device 1 will now be explained in detail.

<Construction Example for Connector>

FIG. 2 is a diagram showing a construction example of a connector 20 of the embodiment. The connector 20 includes a coupling body 200 having one end 201 and another end 202 in the lengthwise direction, and comprising a through-hole 203 running through the center of the one end 201 and the other end 202 at the center of the shaft. The through-hole 203 conducts inflow and/or discharge of fluids (including, for example, liquids such as water, and gases such as air). The coupling body 200 includes a tube catch section 204 that prevents the connecting tube 150 from being inserted too far when the one end 201 is inserted in the connecting tube 150 of the therapeutic substance-carrying unit 10, and that receives the force of pressure contact when the anchoring nut 210 is screwed forward for anchoring to the connecting tube 150, whereby the end 152 of the connecting tube 150 contacts with the one end 204a of the tube catch section 204, serving to closely contact and form an airtight seal between the connecting tube 150 and the coupling body 200. The one end 204a is formed in a tapered manner that increases in diameter from the one end 201 of the coupling body 200 toward the other end 202. This causes the connecting tube 150 to be inserted while spreading out along the tapered form of the tube catch section 204, so that the connecting tube 150 becomes closely adhering with the coupling body 200, thereby allowing leakage of fluid from between the connector 20 and the connecting tube 150 to be prevented.

Figure 2E:
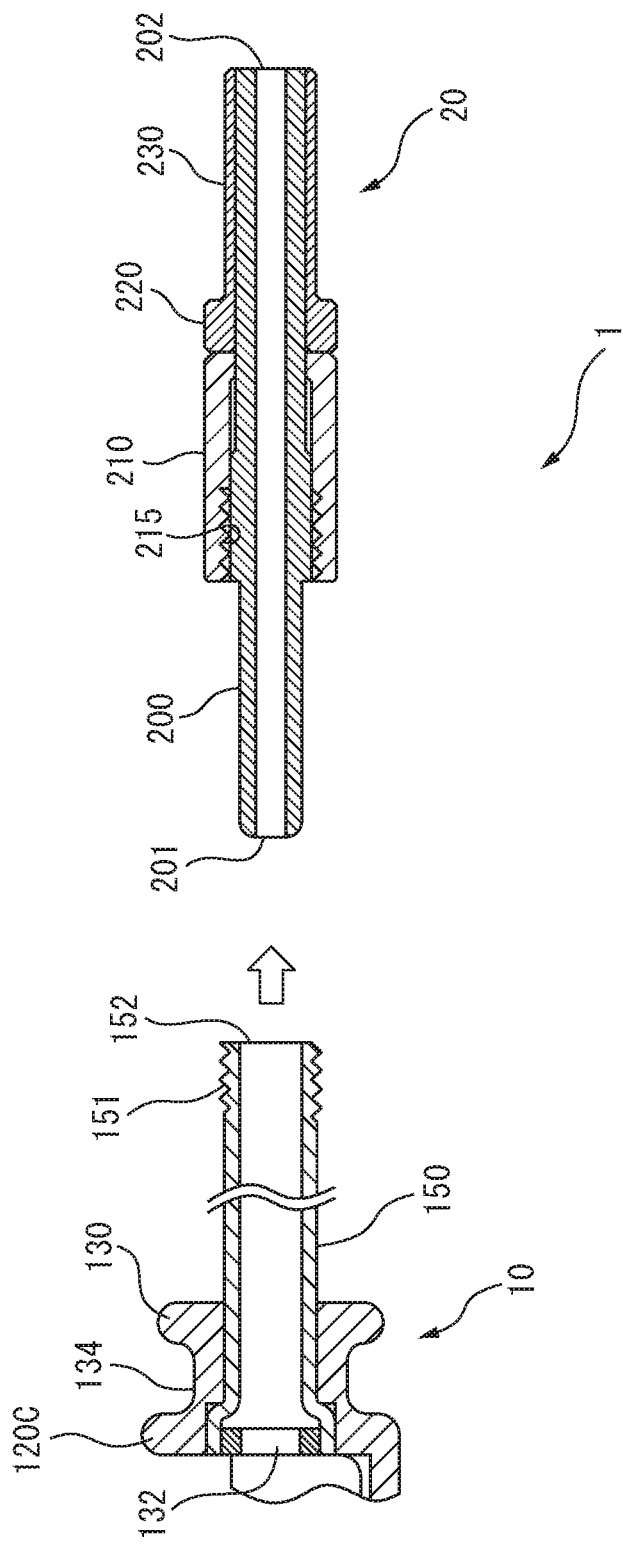
FIG. 2E is a cross-sectional view showing the connector and therapeutic substance-carrying unit of the embodiment.

In addition, the connector 20 includes an anchoring nut 210 through which the coupling body 200 is inserted, there being provided an internal thread 215 in at least a portion of the anchoring nut 210. The anchoring nut 210 comprises a tubular screw part 211, and a collar section 213 that covers one end section of the tubular screw part. The collar section 213 has at its center an insertion hole 214 for insertion of the coupling body 200. Forward screwing of the anchoring nut 210 causes the internal thread 215 to bite into the connecting tube 150 being clamped by the anchoring nut 210 and coupling body 200, cutting a screw into the connecting tube 150 while being anchored. When anchoring of the connector 20 anchored in the connecting tube 150 is released, an internal thread imprint 151 remains in the connecting tube 150 of the therapeutic substance-carrying unit 10, as shown in FIG. 2E. Since the remaining internal thread imprint 151 is a visible indication that the therapeutic substance-carrying unit 10 has been used at least once, from a safety standpoint this can prevent reuse of the therapeutic substance-carrying unit 10.

In addition, the coupling body 200 is provided with a flange section 220 on the other end 202. The outer diameter of the flange section 220 has the same or a smaller diameter than the outer diameter of the anchoring nut 210, and a larger diameter than the insertion hole 214 formed in the collar section 213. This can prevent the anchoring nut 210 from falling out from the coupling body 200. The flange section 220 may be directly bonded to the coupling body 200, or it may be anchored by pressure fitting to the other end of the coupling body 200, as with the nut stopper flange 230, with no particular restriction so long as the construction is such that the anchoring nut 210 does not fall off from the coupling body. There are also no particular restrictions on the thickness of the flange section 220. The material of the coupling body 200 may be any metal or resin (plastic) that is applicable for medical purposes.

The anchoring nut 210 has a knurl structure 212 to prevent slipping of the finger during rotation. The material of the anchoring nut 210 may be any metal or resin (plastic) so long as it is applicable for medical purposes, but it is preferably a metal with hardness since it is necessary to anchor the connecting tube 150 while cutting it with the internal thread 215.

The length and diameter of the connector 20 in the lengthwise direction may be selected as an appropriate length and diameter to allow passage of the curved section 1103 of the forceps channel 1100 when the therapeutic substance conveying device 1 is used together with an endoscope 1000 (described in detail below).

The connector 20, as part of the construction of the invention, lacks the external thread structure of the conventional coupling structure, and has a simple construction comprising 3 parts: the coupling body 200, the anchoring nut 210 and the flange section 220. It is thus possible to provide a connector 20 with a smaller diameter than the diameter of the forceps channel 1100 of the endoscope 1000, and to provide a therapeutic substance conveying device 1 that can be freely detached without the therapeutic substance-carrying unit 10 falling off when used in a biological tract.

<Therapeutic Substance-Carrying Unit>

Figure 3:
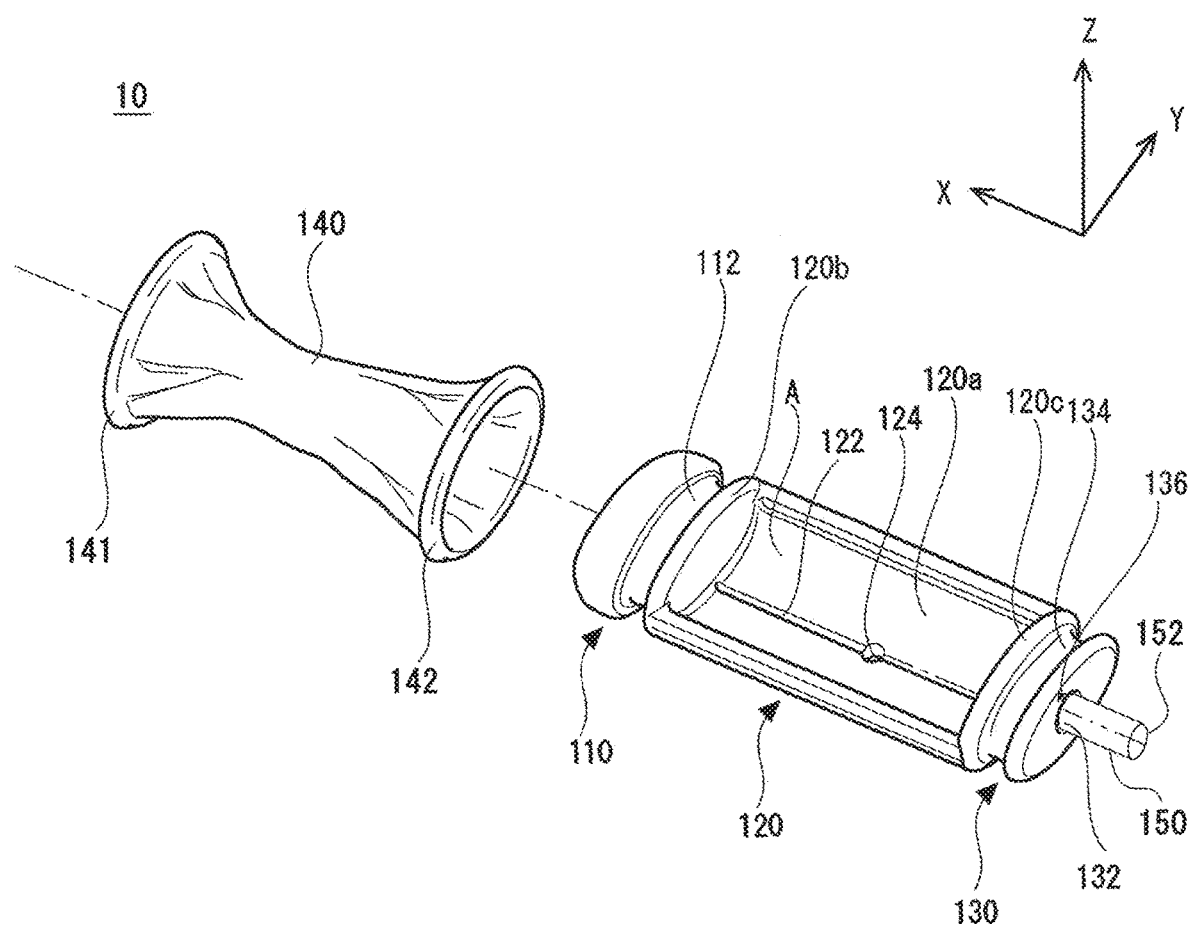
FIG. 3 is a perspective view showing an example of the construction of a therapeutic substance-carrying unit according to the embodiment.

FIG. 3 is a perspective view showing an example of the construction of the body portion 100 and balloon 140 in a therapeutic substance-carrying unit 10 of a therapeutic substance conveying device 1. In FIG. 3, the body portion 100 comprises one end 110 (front end), another end 130 (rear end), and a middle section 120 with a recess A formed between the one end 110 and the other end 130, along the lengthwise direction (the X direction in FIG. 3). The central axis of the one end 110, middle section 120 and other end 130 are coaxial. Between the one end 110 and the middle section 120 there is formed a groove 112 running around the circumferential direction of the body portion 100, and between the other end 130 and the middle section 120 there is formed a groove 134 running around the circumferential direction of the body portion 100.

For this embodiment, the cross-sectional shapes of the one end 110, middle section 120 and other end 130 in the widthwise direction (the Y direction in FIG. 3) are each elliptical, the long axis of the ellipse being oriented in the widthwise direction of the body portion 100 and the short axis being oriented in the height (thickness) direction of the body portion 100 (the Z direction in FIG. 3). The dimension of the body portion 100 in the height direction is therefore shorter than the dimension in the widthwise direction.

For this embodiment, the recess A is formed by forming the middle section 120 as a cylindrical member with an opening. As shown in FIG. 3, the middle section 120 has a half-elliptical cylindrical section 120a with an approximately half-elliptical cylindrical shape, being a shape wherein the peripheral surface on the top half of a hollow-interior elliptic cylinder has been removed, and an elliptical side wall 120b and an elliptical side wall 120c provided on either end of the half-elliptical cylindrical section 120a. The side wall 120b is provided on one side of the half-elliptical cylindrical section 120a at the one end 110, and the side wall 120c is provided on the other side of the half-elliptical cylindrical section 120a at the other end 130 (see FIG. 4). An opening is formed at the top of the middle section 120 (in the height direction), with the inside of the half-elliptical cylindrical section 120a forming the recess A. However, this inner surface shape and outer surface shape of the recess of the middle section 120 is only an example, and there is no limitation to an elliptical peripheral surface.

The one end 110 is formed as an elliptic cylindrical shape with a chamfered leading edge. If the tip of the one end 110 is chamfered, this will help to reduce friction between the body portion 100 and the biological tract when the therapeutic substance-carrying unit 10 is inserted into the biological tract, and to avoid damage to the inner lumen of the biological tract.

The other end 130 has the end face formed as a flat ellipse. At the other end 130, an open hole 132 (an example of a "fluid channel" or "fluid hole") is formed running from the rear edge of the other end 130 up to the side wall 120c, the central axis of the other end 130 running through the open hole 132 (see FIG. 4). One end (the front end) of the connecting tube 150 shown in FIG. 1 is closely fitted to the inner wall of the open hole 132 when inserted into the open hole 132, the connecting tube 150 becoming connected to the body portion 100 and communicating with the inner space S. The connecting tube 150 partially includes a flexible material, wherein at least one end of the connecting tube does not have an external thread structure. When connected with the connector 20 mentioned above, the connecting tube 150 must be anchored while having a screw cut into it by the connector 20, and it must therefore be flexible. Furthermore, if the connecting tube 150 is flexible, when the therapeutic substance-carrying unit 10 is introduced into a biological tract the insertion can be accomplished without catching on curved sections or concavoconvex sections of the biological tract. The material of the connecting tube 150 is not restricted so long as it is flexible and is a material suitable for medical use, and examples include polytetrafluoroethylene (PTFE) and silicone rubber, etc.

The open hole 132 is formed to the same diameter as the outer diameter of the connecting tube 150, from the rear edge of the other end 130 to a prescribed location. The open hole 132 is also opened with a smaller diameter than the outer diameter of the connecting tube 150, from the prescribed location to the side wall 120c. The connecting tube 150 is anchored by being pushed in from the rear edge of the open hole up to the prescribed location. The connecting tube 150 and the inner surface of the open hole 132 are anchored by an adhesive or the like (see FIG. 4).

At the rear edge of the other end 130 there is provided a mark 136 indicating the location of the recess A of the middle section 120. The mark 136 is formed at the (elliptical) end face of the other end 130 using a pen or the like on the side where the recess A is provided (the top side for this embodiment), above the short axis of the ellipse. The mark 136 may also be formed by a partial notch cut out at a prescribed location. Alternatively, the mark 136 may be formed during molding of the body portion 100. By providing the mark 136 it is possible to easily recognize the location of the recess A even when the body portion 100 is viewed directly from the rear (where the recess A cannot be seen).

The groove 112 and groove 134 are formed to receive the one end 141 and the other end 142 of the balloon 140 covering the middle section 120 (as described in detail below). A groove 122 is formed in the lengthwise direction at the bottom face of the recess A. At approximately the center of the bottom face of the recess A there is also formed a through-hole 124 running through the bottom face of the recess A and the outer surface of the middle section 120. The groove 122 and through-hole 124 are formed for suitable discharge of gas from the inner space S that is formed by the body portion 100 and the balloon 140 (FIG. 4) (as described in detail below).

The material used for the body portion 100 may be any metal or resin (plastic) that is applicable for medical purposes. For example, the body portion 100 may be formed by joining multiple parts, or it may be molded in an integral manner with a resin material. Alternatively, the body portion 100 may be integrally formed using a medical 3D printer material.

For this embodiment, the balloon 140 is formed in a tubular fashion using an elastic member (for example, medical rubber such as latex), the one end 141 and other end 142 thereof being in the form of rings surrounded with elastic members. The dimension of the balloon 140 in the lengthwise direction is shorter than the dimension of the body portion 100 in the lengthwise direction, and the balloon 140 covers the body portion 100 as the body portion 100 passes through the interior of the balloon 140, with the one end 110 and other end 130 extending (protruding) out from the one end 141 and the other end 142 of the balloon 140, respectively.

The one end 141 of the balloon 140 is received in the groove 112 while the other end 142 is received in the groove 134. This produces a state in which the balloon 140 covers the middle section 120 including the recess A. Moreover, by receiving the one end 141 and other end 142 in the grooves 112, 134, it is possible to prevent the one end 141 and other end 142 from acting in a direction that might interfere with movement of the therapeutic substance-carrying unit 10 in a biological tract (by being caught on the inner wall of the biological tract, for example). In addition, if the one end 141 and other end 142 are in contact with the biological tract it will be possible to avoid shifting of the anchoring position of the balloon 140 with respect to the body portion 100. The depths of the grooves 112, 134 are also adjusted to the thicknesses of the one end 141 and other end 142. By adjusting the depths of the grooves 112, 134 to the thicknesses of the one end 141 and other end 142 (the thickness of the portions surrounded by the elastic members), it is possible to avoid formation of level differences between the one end 141 and other end 142 received by the grooves 112, 134, and the perimeters of the grooves 112, 134. A lack of level differences can help prevent the one end 141 and other end 142 from acting in a direction that might interfere with movement of the therapeutic substance conveying device 1 in a biological tract.

The portion of the balloon 140 further inward than the one end 141 is bonded and anchored to the body portion 100 (the bottom face of the groove 112) with an adhesive or the like, and the portion further inward than the other end 142 is bonded and anchored to the body portion 100 (the bottom face of the groove 134) with an adhesive or the like. The means for bonding the balloon 140 is not restricted to an adhesive, and for example, medical thread (such as suture thread), or instead of thread, a fastener or O-ring, may be used.

Figure 4:
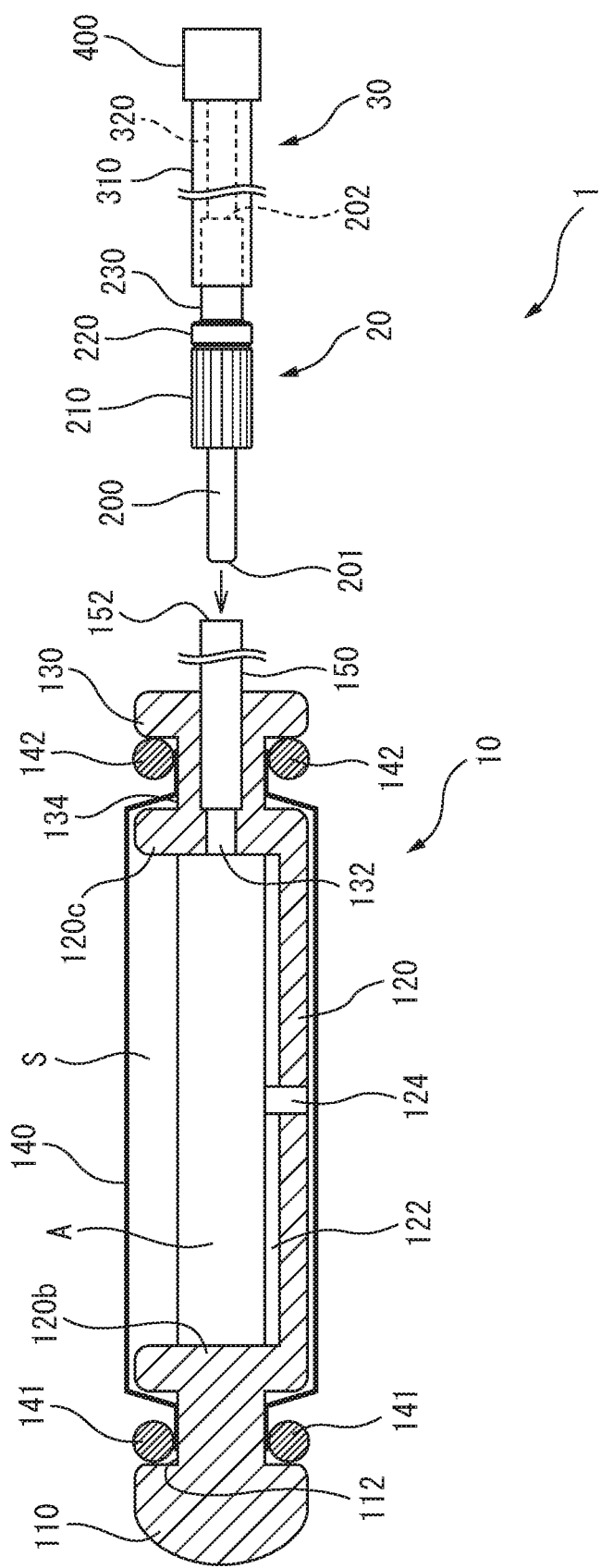
FIG. 4 is a cross-sectional view showing an example of the construction of a therapeutic substance conveying device according to this embodiment.

FIG. 4 is a diagram schematically showing a cross-section of the state in which the balloon 140 is anchored to the body portion 100 shown in FIG. 3, being cut on a plane in the height direction (Z direction) that includes the central axis of the body portion 100, before the air supply/discharge tube 30 is connected to the connecting tube 150 of the therapeutic substance-carrying unit 10. FIG. 5 is a diagram showing the change from the state illustrated in FIG. 4 to a state of discharge of the inner space, the connecting tube 150 and air supply/discharge tube 30 being connected through the connector 20. Anchoring the one end 141 and other end 142 of the balloon 140 in a manner closely fitting with the body portion 100 causes both ends of the balloon 140 to become sealed, forming an inner space S on the inside of the balloon 140. The pressure inside the inner space S can be controlled by introduction and discharge of air (an example of a "fluid") through the air supply/discharge tube 30 and the open hole 132 (air supply or discharge).

FIG. 4 shows the state without supply or discharge into the inner space S. In this state, the portion of the balloon 140 covering the recess A becomes situated above the recess A due to its own elasticity (flexibility). When a syringe (inflation means 400) is connected to the air supply/discharge tube 30 and the piston of the syringe is pulled, air is discharged from the inner space S, producing a negative pressure inside the recess A. When this occurs, as shown in FIG. 5, the portion covering the recess A of the balloon 140 becomes drawn into the recess A, finally reaching a state of contact with the bottom face of the recess A.

The reason for forming the groove 122 will now be explained. When the balloon 140 is drawn into the recess A by discharge of the inner space S, and a portion thereof becomes closely fitted with the bottom section of the recess A, air in the inner space S1 further toward the front end than the closely fit section may not be able to move to the open hole 132. By forming the groove 122, however, air in the inner space S1 can move to the open hole 132 through the groove 122 and the inner space S2 at the rear edge.

This allows proper discharge of air in the inner space S, and allows the balloon 140 to be flat in the recess A when discharge is complete. The shape of the groove 122, however, is optional.

Figure 5A:
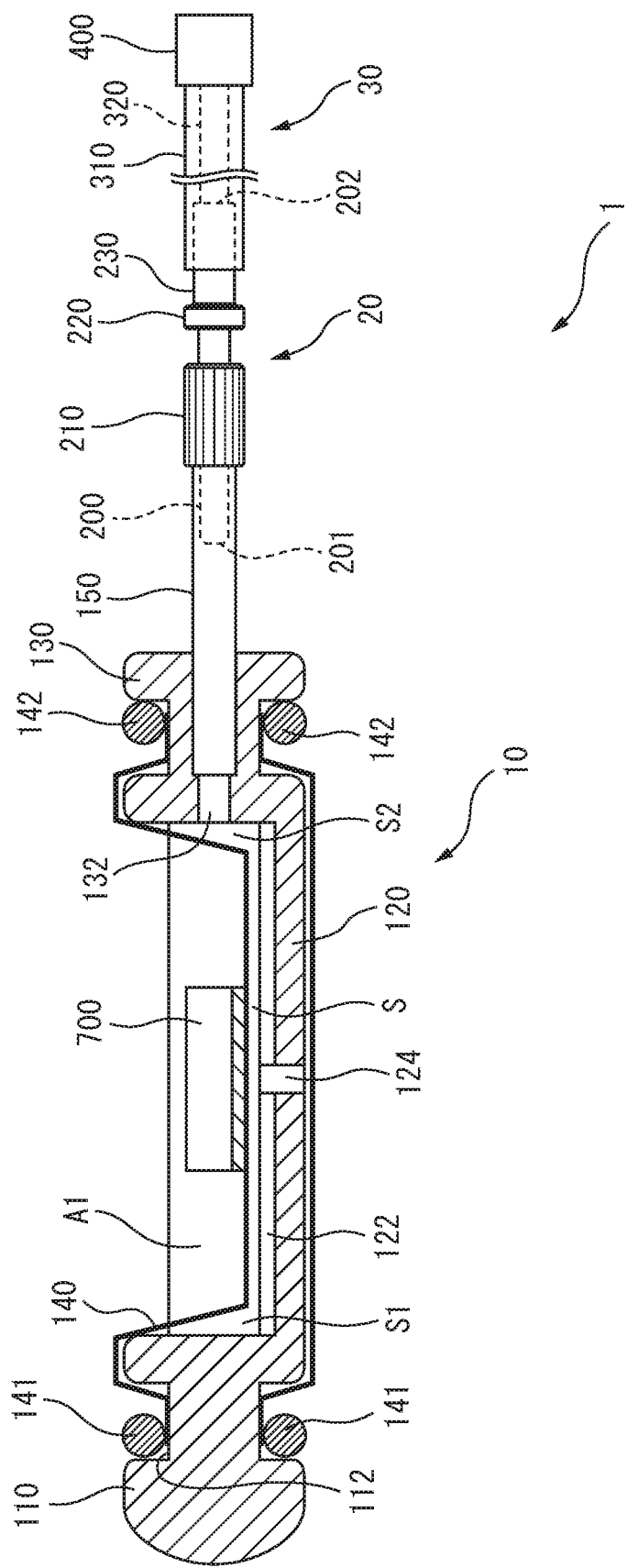
FIG. 5A is a diagram showing an example of the construction of a therapeutic substance conveying device according to the embodiment.

As mentioned above, the recess A1 of the therapeutic substance-carrying unit 10 formed when a portion of the balloon 140 is drawn into the recess A is used as the carrying part that carries the therapeutic substance 700 (see FIG. 5A). The therapeutic substance 700 may be a sheet-like therapeutic substance, for example, such as a cell sheet, or a drug-coated sheet, or a viscous therapeutic substance. The therapeutic substance 700 may also include a therapeutic substance (such as a drug) that is in a form other than a sheet.

The reason for forming the through-hole 124 will now be explained. Specifically, the balloon 140 begins to expand as air continues to be fed into the inner space S, the air in the inner space S enveloping the outer surface of the middle section 120, and the balloon 140 thereby separates from the outer surface of the middle section 120, finally swelling into the shape of a barrel (see FIG. 5B). There is no particular restriction on the manner of expansion of the balloon 140 during this time, but it is preferably larger at the leading edge of the device.

When air is subsequently discharged from the inner space S, the balloon 140 contracts. One may consider the situation where no through-hole 124 is present. If this is the case, then air in the inner space S below the middle section 120 (on the outer surface side) will move toward the open hole 132 through the recess A (opening). Consequently, in the state where the inner surface of the balloon 140 is obstructing the opening (recess A) during contraction of the balloon 140, air remaining on the (lower) outer surface side of the middle section 120 will no longer be able to escape.

In this state, the upper end (recess A side) of the balloon 140 becomes pulled by the amount by which the balloon 140 is being expanded at the lower end, and therefore, depending on the conditions, a state can potentially result in which a part of the balloon 140 is not sufficiently drawn into the recess A even when discharge from the inner space S continues. By providing the through-hole 124, however, air enveloping the outer surface side of the middle section 120 can move to the open hole 132 through the through-hole 124, thereby allowing air to be properly discharged from the inner space S of the balloon 140. The through-hole 124, however, is optional.

<Therapeutic Substance-Carrying Unit (Modified Example)>

Figure 6A:
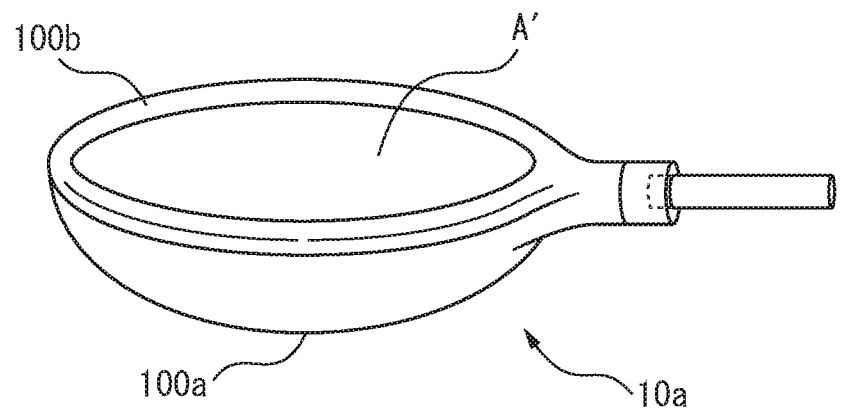
FIG. 6A is a perspective view showing a modified example of the construction of a therapeutic substance-carrying unit according to the embodiment.
Figure 6B:
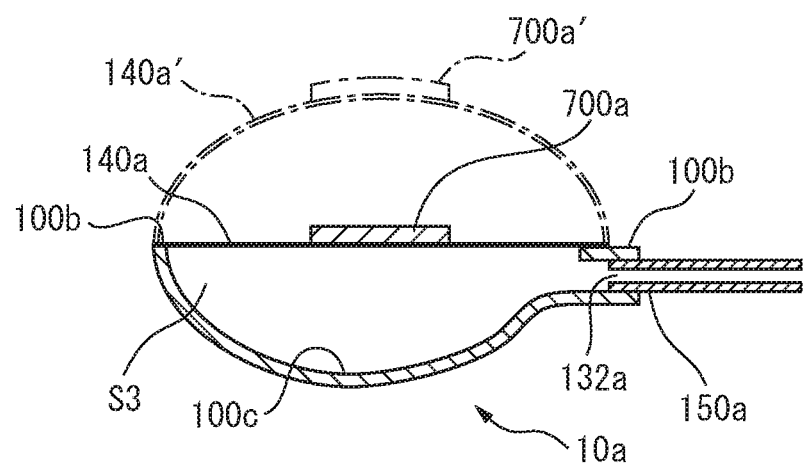
FIG. 6B is a cross-sectional view showing a modified example of the construction of a therapeutic substance-carrying unit according to the embodiment.

FIG. 6 is a set of diagrams showing a modified example of the therapeutic substance-carrying unit 10 of FIG. 1 (also to be referred to as "therapeutic substance-carrying unit 10a"). For this embodiment, the shape of the body portion 100a of the therapeutic substance-carrying unit 10a is an approximate half-spheroid shape which is half of an approximately spheroid hollow shape, or an approximate half-egg shape which is half of an approximate (hollow) egg-shape, in the lengthwise direction, the interior being the shape of the recess A'. An approximate spheroid is a body of rotation obtained from an ellipse, with the long axis or short axis as the rotation axis. According to the invention there is no limitation to an elliptical body of rotation, and for example, an approximate half-egg shape obtained by halving a polarized sphere, such as an approximate egg-shape, is also included. The edge 100b surrounding the opening of the body portion 100a has a closely fitted and anchored flat elastic membrane 140a, whereby the recess A' of the body portion 100a is covered, the inner space S3 being formed by the recess A' and the elastic membrane 140a. The bottom face portion 100c of the recess A' may be curved or flat. The elastic membrane 140a is an elastic member (for example, medical rubber such as latex). A portion of the body portion 100a is provided with an open hole 132a to which the connecting tube 150a is connected, allowing fluid to be supplied and discharged to and from the inner space S3. Similar to the therapeutic substance-carrying unit 10 of FIG. 1, the therapeutic substance-carrying unit 10a of this embodiment is also connected with the air supply/discharge tube 30 at the connecting tube 150a through the aforementioned connector 20, to obtain a therapeutic substance conveying device (not shown). FIG. 6B shows a cross-sectional view of FIG. 6A in the long axis direction. This is an example in which the inflation means 400 is further connected to an air supply/discharge tube 30 (not shown), and air (an embodiment of a fluid) feeds into the inner space S3, expanding the elastic membrane 140a (the dotted line 140a' in FIG. 6B). This allows the therapeutic substance 700 carried on the elastic membrane 140a to be applied to the affected part of a biological tract.

Figure 6C:
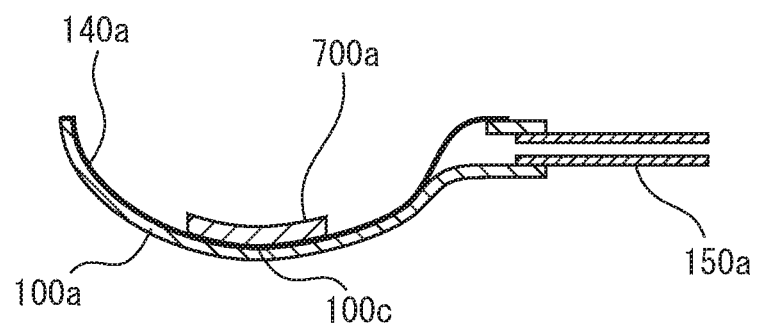
FIG. 6C is a cross-sectional view showing a modified example of the construction of a therapeutic substance-carrying unit according to the embodiment.

FIG. 6C shows the form of the elastic membrane 140a when air has been discharged from the inner space S3 by the connected inflation means 400, similar to FIG. 5A above. When the inner space S3 is brought to negative pressure, the elastic membrane 140a becomes closely fit along the inner wall of the recess A' of the body portion 100a. This allows the therapeutic substance 700 carried on top of the elastic membrane 140a to be conveyed to the affected part without contacting the inner lumen of the biological tract. Since the elastic membrane 140a covers only the opening of the body portion 100a for this embodiment, only the elastic membrane 140a on one side of the therapeutic substance-carrying unit 10a is inflated. Consequently, it is easy to ensure a visual field when the elastic membrane 140a has been expanded in the biological tract.

There are no particular restrictions on the method of anchoring the elastic membrane 140a on the edge 100b of the body portion 100a, and it may be bonded with an adhesive, for example.

<Air Supply/Discharge Tube>

Figure 7:
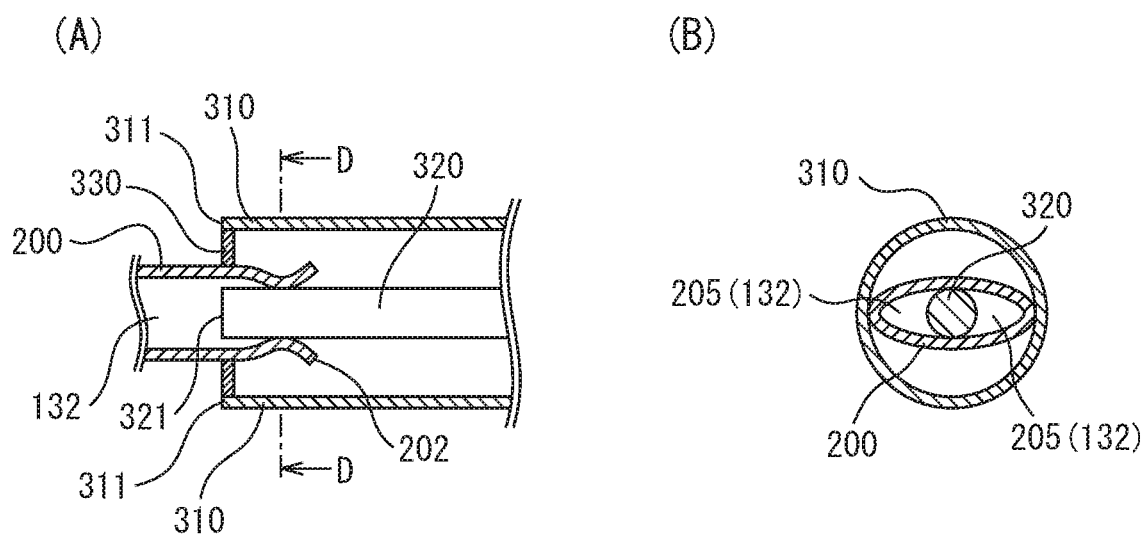
FIG. 7 is a pair of diagrams showing a connecting unit between the connector and air supply/discharge tube of the embodiment. (A) is a diagram showing the connecting unit between the connector and the air supply/discharge tube. (B) is a diagram showing a cross-sectional view of (A) along D-D'.

FIG. 7 shows a connecting unit between the air supply/discharge tube 30 and the connector 20. As mentioned above, the air supply/discharge tube 30 is used for supply and discharge of air for pressure control of the inner space S. The air supply/discharge tube 30 is also used to apply rotary force (torque) to the therapeutic substance-carrying unit 10 in the circumferential direction. Therefore, the air supply/discharge tube 30 preferably comprises a material that is flexible enough to allow torque to efficiently reach the therapeutic substance-carrying unit 10 connected via the connector 20, while still being somewhat rigid.

For this embodiment, a torque wire 320 is used in part of the air supply/discharge tube 30 in order to apply rotary force to the therapeutic substance-carrying unit 10 in the circumferential direction. The torque wire 320 is a type that is used as a catheter guide wire, and a metal wire may be used, for example. The torque wire 320 may have a hollow structure, or it may lack a hollow structure. For this embodiment, the torque wire 320 used is a non-hollow one, the diameter being a smaller diameter than the inner diameter of the coupling body 200 of the connector 20, and a sufficient diameter to allow fluid to pass through the through-hole 203 of the coupling body 200.

The end portion 321 of the torque wire 320 of this embodiment is inserted into the through-hole 203 at the other end 202 of the coupling body 200, while pressing against part of the coupling body 200 (see FIG. 7(B)). This causes deformation of part of the coupling body 200, and clamping and anchoring of the torque wire 320. During this time, both sides (or optionally only one side) of the pressed and anchored torque wire 320 form a flow passage hole 205

(part of the open hole 132) through which fluid can pass. The fluid passes in and out through this flow passage hole 205. Since the torque wire 320 does not have a hollow structure for this embodiment, fluid cannot pass through the interior, and therefore it is necessary to have the supply and discharge tube 310 through which the torque wire 320 has been inserted. On the outer side of the torque wire 320, a supply and discharge tube 310 is used that is composed of a material that is flexible and does not interfere with rotary manipulation in the circumferential direction of the torque wire 320. The supply and discharge tube end portion 311 of the supply and discharge tube 310 is sealed with a sealing tube material 330 having a diameter that is smaller than the inner diameter of the supply and discharge tube 310 and larger than the outer diameter of the coupling body 200 of the connector 20, using an adhesive or the like, so that fluid passing through the interior of the supply and discharge tube does not leak out. An O-ring or the like may also be used instead of the sealing tube material 330. For this embodiment, the material of the supply and discharge tube 310 and the sealing tube material 330 may be a material that is applicable for medical purposes and is flexible, and that has low friction when passing through the forceps channel 1100, such as a resin tube, an example of which is a polytetrafluoroethylene (PTFE) tube. A PTFE tube is only an example, however, and resin tubes other than PTFE may be used.

The same structure used for connection between the air supply/discharge tube 30 and the coupling body 200 (not shown) may also be employed at the leading edge of the air supply/discharge tube 30 that is to be connected to the inflation means 400 described below. For example, when a syringe is to be used as the inflation means 400, the tip section of the torque wire 320 may be inserted at the tip section of a non-beveled needle and pressed in the same manner as the end portion 321 for anchoring of the tip section of the torque wire 320, sealing the region between the tip section of the supply and discharge tube 310 and the non-beveled needle with a sealing tube material 330. This will allow an air supply/discharge tube 30 to be provided that can apply torque without leakage of the fluid.

<Air Supply/Discharge Tube (Modified Example)>

While not shown here, a stainless steel tube having a hollow structure may be used as an example of a metal tube for the air supply/discharge tube 30, as a modified example of the invention. However, the material of the air supply/discharge tube 30 is not restricted (it may be a material other than a metal), so long as the desired flexibility and rigidity can be obtained. Since the stainless steel tube has a hollow structure in this case, the end portion may be directly inserted into the through-hole 203 of the coupling body 200 and anchored by pressure fitting. When the outer diameter of the stainless steel tube is smaller (narrower) than the outer diameter of the wire of wire driven forceps commonly used in endoscopic surgery, a cover tube may be provided on the outer side of the stainless steel tube, in order to produce a more satisfactory feel during use by the user of the therapeutic substance conveying device 1 (the doctor) (that is to say, the feel of the wire held by the doctor), in order to improve operativity with minimal discomfort. In other words, the cover tube has an inner diameter dimension that can house the stainless steel tube and an outer diameter dimension that allows passage of the forceps channel 1100 of the endoscope 1000.

For this modified example, the stainless steel tube used may have an outer diameter of 0.6 mm to 0.9 mm, and the cover tube used may have an outer diameter of 2.5 mm. The outer diameter dimension of the cover tube is approximately the same as the outer diameter of forceps wire used in common endoscopic surgery. The preferred range for the outer diameter dimension of the cover tube will differ depending on the forceps channel of the endoscope, but it may be 2.0 mm to 2.6 mm, for an endoscope having a 2.8 mm forceps channel, for example. The material of the cover tube may be a material that is applicable for medical purposes and is flexible, and that has low friction when passing through the forceps channel 1100, such as a resin tube, an example of which is a polytetrafluoroethylene (PTFE) tube. A PTFE tube is only an example, however, and resin tubes other than PTFE may be used.

Example of Use

Figure 8:
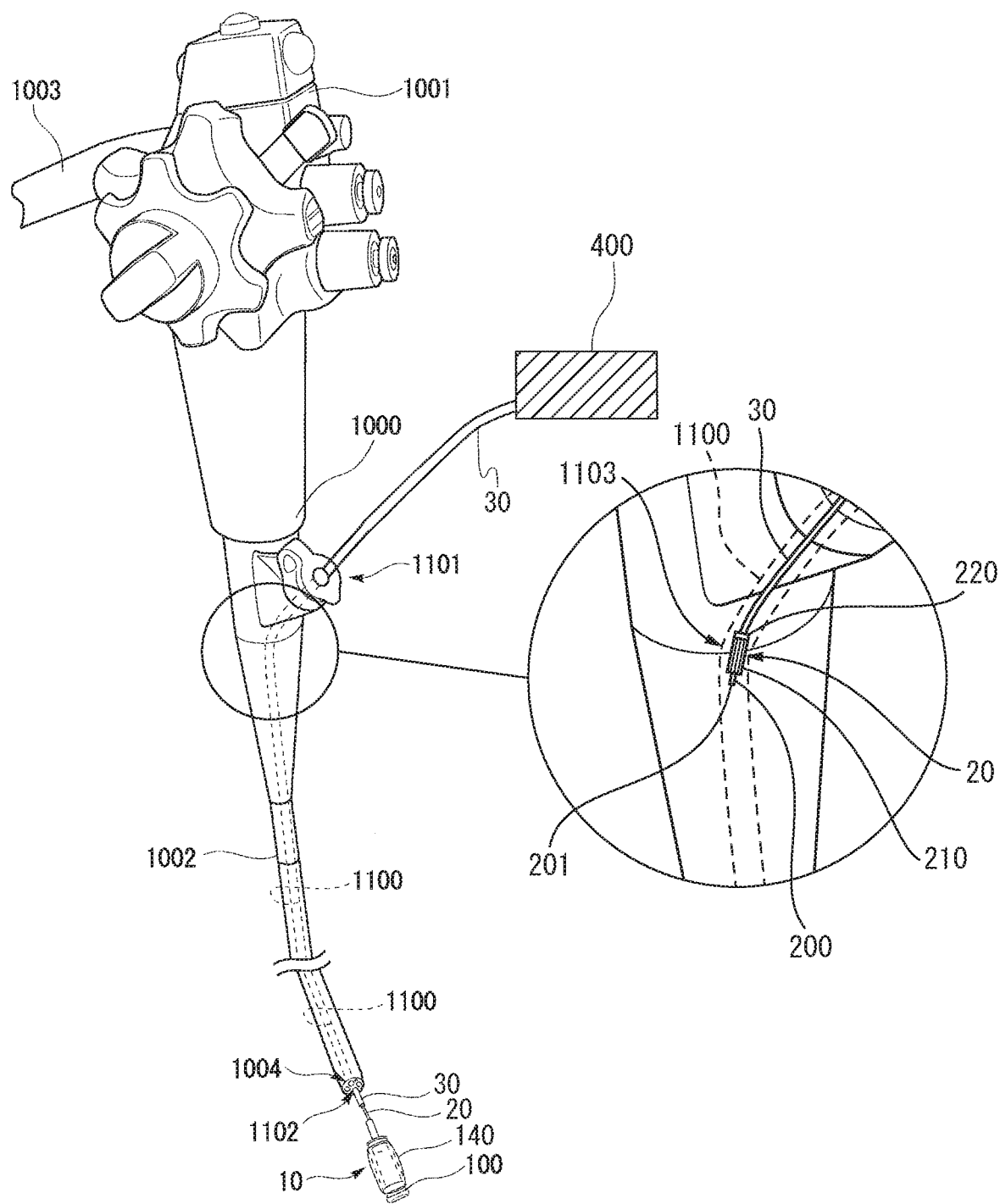
FIG. 8 is a diagram illustrating the use of a therapeutic substance conveying device and an endoscope system in combination.

An example of using the therapeutic substance conveying device 1 will now be described. The therapeutic substance-carrying unit 10 is used in combination with an endoscope system. FIG. 8 is a diagram illustrating the use of a combination of the therapeutic substance-carrying unit 10 with an endoscope system.

In FIG. 8, the endoscope 1000 (videoscope) comprises an operating unit 1001 provided with an angle knob or button, which is operated by the skill of a doctor, an insertion part 1002 that is inserted into the patient's body, and a connecting unit 1003 (universal cord). At the end face of the insertion part 1002 there is provided an irradiation lens that irradiates illumination light, and an objective lens that focuses reflected illumination light to an image sensor inside the insertion part 1002 (CCD, CMOS: not shown).

The connecting unit 1003 is connected to a video processor (not shown) that converts the electrical signal obtained at the image sensor into an image signal and displays it on a display unit (not shown), and a light source device (not shown) that transmits light from the light source to the tip of the insertion part 1002 (illumination lens).

In addition, in the interior of the endoscope 1000 there is formed a forceps channel 1100 to pass forceps (wire) from the operating unit 1001 through to the insertion part 1002. A forceps channel entry hole 1101 is formed on the outer surface of the operating unit 1001, and a forceps channel exit hole 1102 (forceps hole) is formed at the front end of the insertion part 1002.

The therapeutic substance conveying device 1 inserts the tip of the air supply/discharge tube 30 to which the therapeutic substance-carrying unit 10 is not connected (the connector 20 being connected to the tip section) (the connector 20) into the forceps channel entry hole 1101, and conveys the tip up to the forceps channel exit hole 1102. The diameter and length of the connector 20 must be a diameter and length allowing it to pass through the curved section 1103 of the forceps channel. For this example, the diameter is 2.6 mm and the length is 18 mm.

When the tip of the air supply/discharge tube 30 (the connector 20) has protruded out from the forceps channel exit hole 1102, the connector 20 and connecting tube 150 are connected to allow the therapeutic substance-carrying unit 10 to be fitted on the air supply/discharge tube 30 (the therapeutic substance-carrying unit 10 being in a state anchored to the tip of the air supply/discharge tube 30).

Figure 9:
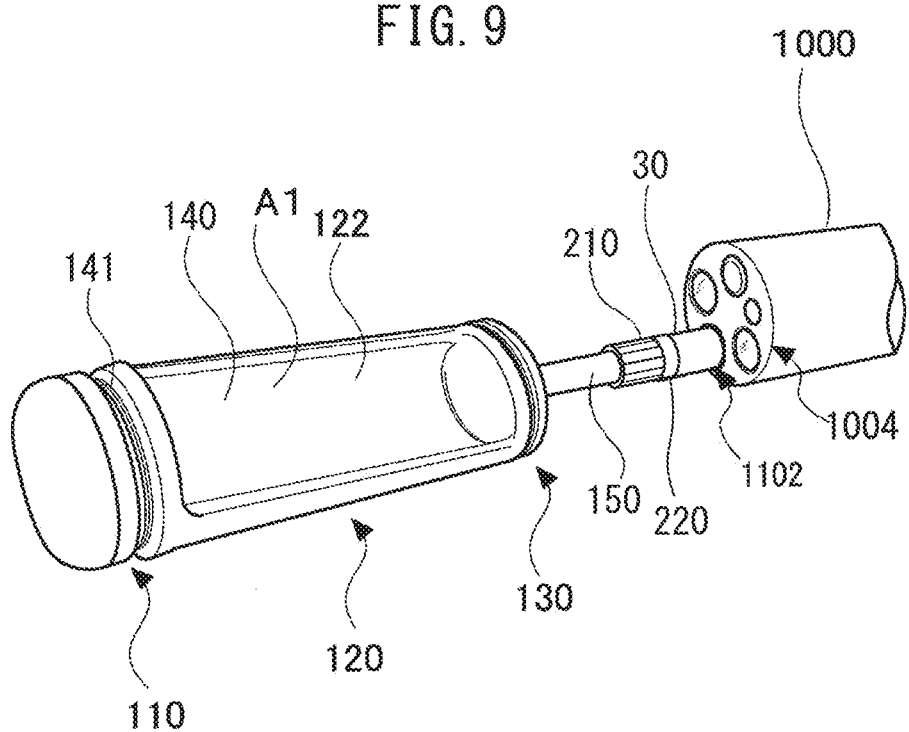
FIG. 9 is a diagram showing an example of the construction of a therapeutic substance conveying device according to an embodiment.

Next, the piston of the inflation means 400 (syringe) connected to the end of the air supply/discharge tube 30 is pulled to discharge air from the inner space S. This forms a recess A1, to be used as the carrying part, on the surface of the balloon 140 that has been drawn into the recess A. The resulting state is as shown in FIG. 9.

Figure 10:
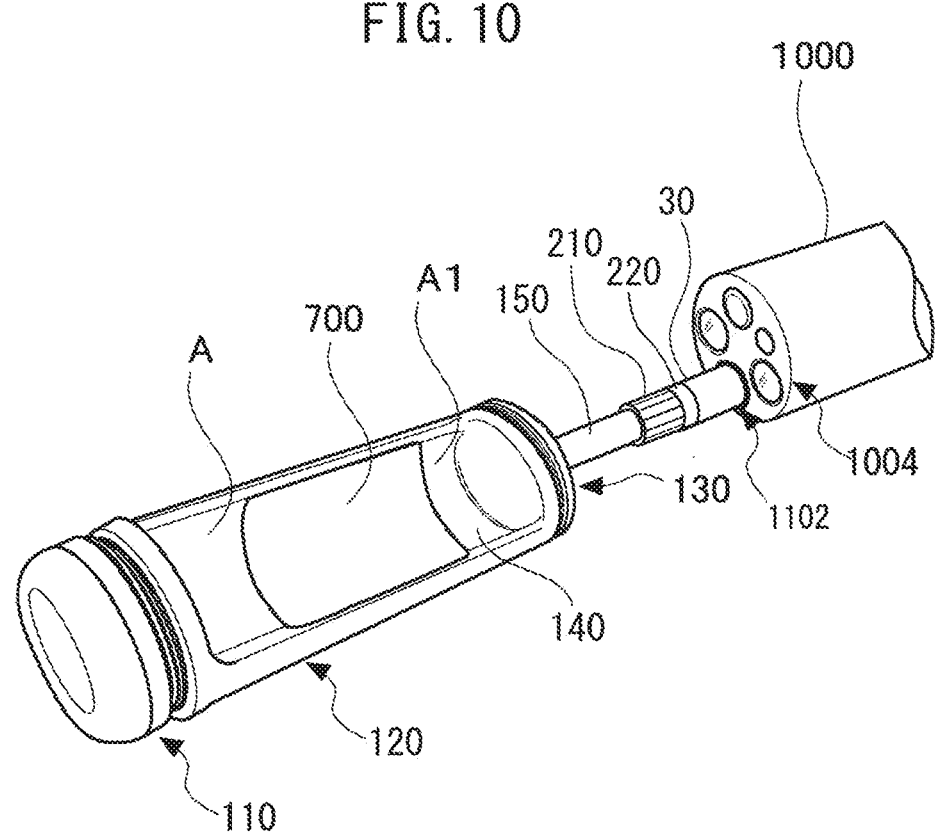
FIG. 10 is a diagram showing an example of the construction of a therapeutic substance conveying device according to an embodiment.

The doctor or doctor assistant then places the appropriate therapeutic substance 700 on the recess A1. This embodiment assumes that the therapeutic substance 700 is a cell sheet (an example of a "sheet-like therapeutic substance"). The therapeutic substance 700 is carried on the surface of the recess A1 in a spread-out state (see FIG. 10). However, the therapeutic substance 700 may be set before discharge of air from the inner space S, and the therapeutic substance 700 drawn into the recess A by discharge of the inner space S. Naturally, placing the therapeutic substance 700 after forming the recess A1 by discharge from the inner space S will help avoid errors in visually judging the carrying location, as well as run-out of the therapeutic substance 700 from the recess A1.

The doctor then inserts the body portion 100 and the insertion part 1002 into a sheath that has been preset in the biological tract of the patient (guide tube: not shown), and sends the insertion part 1002 (body portion 100) to a location near the tip of the sheath. It is assumed that irradiation of illumination light and image display on the display unit have been continuous up to this point. In other words, it is assumed that an image of the body portion 100 as seen from behind is picked up by an image sensor and displayed on the display unit.

Next, the doctor grips the air supply/discharge tube 30 (hereunder referred to as "operation tube") and sends the operation tube through the forceps channel 1100, so that the body portion 100 separates from the tip section 1004 of the insertion part 1002 and eventually exits the sheath.

Figure 11:
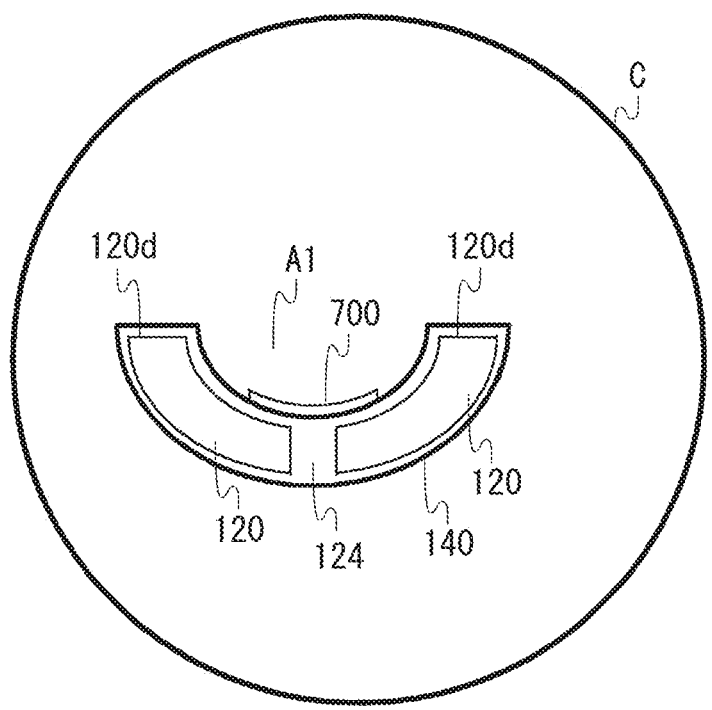
FIG. 11 is a diagram showing an example of the use of a therapeutic substance conveying device according to an embodiment.

FIG. 11 is a diagram schematically showing the therapeutic substance-carrying unit 10 that has been set in a biological tract C (after having left the sheath). FIG. 11 shows the state of the therapeutic substance-carrying unit 10 in the biological tract C while the therapeutic substance 700 (cell sheet) is being conveyed. The therapeutic substance 700 is carried on the bottom face of the recess A1 formed by drawing in the balloon 140. Thus, the inner wall of the biological tract C surrounding the recess A1, and the tip of the sheath, only contact with the top edge portion 120d of the middle section 120, and are less likely to contact the therapeutic substance 700 in the recess A1. This minimizes contact of the therapeutic substance with the biological tract.

Figure 12:
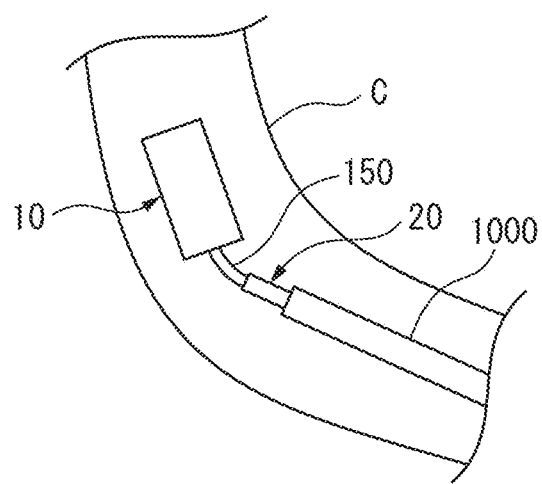
FIG. 12 is a diagram showing an example of the use of a therapeutic substance conveying device according to an embodiment.

FIG. 12 is a diagram schematically showing the therapeutic substance conveying device 1 being used together with an endoscope system, as it passes through a curved section of a biological tract C. By forming the connecting tube 150 of the therapeutic substance-carrying unit 10 using a flexible material, it can smoothly pass through even curved sections (or irregular sections) of the biological tract C.

Next, the therapeutic substance-carrying unit 10 on which the therapeutic substance 700 is carried reaches a location near the affected part AP (see FIG. 14), and the doctor refers to the image displayed on the display unit while confirming that the recess A1 (therapeutic substance 700) is facing the affected part AP. If at this time the therapeutic substance 700 is not facing the affected part AP, the doctor grips the operation tube (the air supply/discharge tube 30 on which the supply and discharge tube 310 is fitted), applying torque to the operation tube by twisting the operation tube to rotate the body portion 100 in its circumferential direction.

When the therapeutic substance 700 reaches a state in which it is facing the affected part AP, the doctor pushes the piston of the inflation means 400 (syringe) to introduce air into the inner space S.

Figure 14:
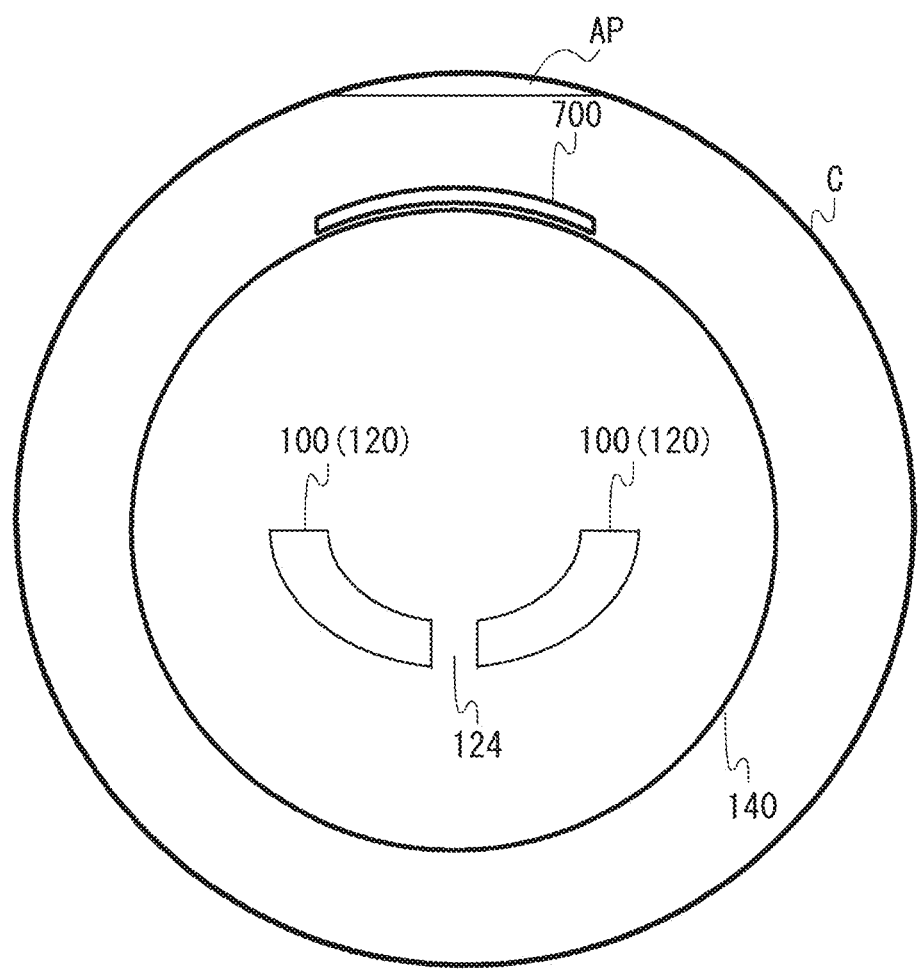
FIG. 14 is a diagram showing an example of the use of a therapeutic substance conveying device according to an embodiment.

Thus, as shown in FIG. 14, air is introduced into the inner space S formed by the balloon 140 and the body portion 100, and the balloon 140 expands. During this time, as shown in FIG. 5B, the bottom face of the recess A and the outer circumference of the middle section 120 are in communication via the through-hole 124. Consequently, air that has been drawn in through the open hole 132 can pass through the through-hole 124 toward the outer surface side of the middle section 120, such that introduction of air to the outside of the middle section 120 takes place in a smooth manner.

FIG. 14 is a diagram showing an example where the balloon closely fitted with the main body has been expanded. The portion of the balloon 140 that was in contact with the therapeutic substance 700 before expansion spreads out by expansion of the balloon 140, creating a more easily detachable state from the surface of the balloon 140 than before the expansion. When the therapeutic substance 700 contacts with the affected part AP in this state, since the affected part AP is moist due to the body fluids, the therapeutic substance 700 separates from the balloon 140 by surface tension and is applied onto the affected part AP. After the therapeutic substance 700 has been situated at the affected part AP, the air in the inner space S is discharged by the inflation means 400 and the balloon 140 contracts. When it has been confirmed that the balloon 140 has contracted to a degree allowing it to be received into the sheath, the therapeutic substance-carrying unit 10 is conducted out of the body together with the insertion part 1002 of the endoscope 1000, and recovered.

When the site where the therapeutic substance 700 is to be applied is large, it may be necessary to use several therapeutic substances 700 (or several dozen, depending on the case). The therapeutic substance-carrying unit 10 that was previously expanded has potentially been in contact with various sites inside and outside of the biological tract and may be contaminated. Therefore, by preparing several therapeutic substance-carrying units 10 with therapeutic substances set on balloons 140 beforehand, the therapeutic substance-carrying units 10 may be exchanged by simple detachment from the connector 20. Moreover, if each therapeutic substance-carrying unit 10 is in a disposable single-use form, it is possible to consistently carry out treatment in a hygienic manner, which is also preferred for the patient, from the viewpoint of preventing infection and the like. According to this embodiment of the invention, connection with the connecting tube 150 by the connector 20 causes an internal thread imprint 151 (FIG. 2E) to remain in the connecting tube 150, and therefore reuse of the therapeutic substance-carrying unit 10 in which the internal thread imprint 151 has been formed is prevented, and safety is ensured.

The example of use described above included the use of a sheath (guide member), but optionally the therapeutic substance-carrying unit 10 and insertion part 1002 may be inserted into the biological tract without using a sheath (guide member).

Function and Effect of the Present Embodiment

According to the present embodiment, it is possible to provide a therapeutic substance conveying device that prevents contact of the therapeutic substance with other objects in a biological tract, while preventing the therapeutic substance-carrying unit from falling off into the biological tract, and wherein the therapeutic substance-carrying unit is detachable from the air supply/discharge tube. Specifically, the therapeutic substance 700 is carried in the recess A1 formed by drawing in a portion of the balloon 140 into the recess A of the body portion 100, and is conveyed within a biological tract. This can reduce the risk of the inner lumen of the biological tract contacting with the therapeutic substance 700 in the recess A1. In other words, contact between the therapeutic substance 700 and other objects can be substantially reduced. This allows the therapeutic substance 700 to be pressed onto the affected part in a suitable condition (for example, the cell sheet can be applied onto the affected part), so that a desirable treatment effect can be expected. Furthermore, since the therapeutic substance-carrying unit 10 is reliably anchored by the connector 20, it is possible to prevent the therapeutic substance-carrying unit 10 from falling off from the air supply/discharge tube 30 when the therapeutic substance conveying device 1 of the invention has been applied to a biological tract. In addition, the therapeutic substance-carrying unit 10 can be easily detached from the air supply/discharge tube 30, allowing only the therapeutic substance-carrying unit 10 of the therapeutic substance conveying device 1 to be exchanged, and consequently shortening the treatment time and helping to guarantee safety (sterility).

Moreover, according to this embodiment, a mark 136 is provided on the rear edge of the other end 130 so that the direction in which the recess A is formed can be ascertained even when the recess A1 is not visible in the image taken of the body portion 100 from behind.

Moreover, this embodiment has a groove 122 formed to allow discharge of air from the inner space S to be carried out in a satisfactory manner. This embodiment also has a through-hole 124 formed to allow discharge of air from the inner space S to be carried out in a satisfactory manner.

Figure 13:
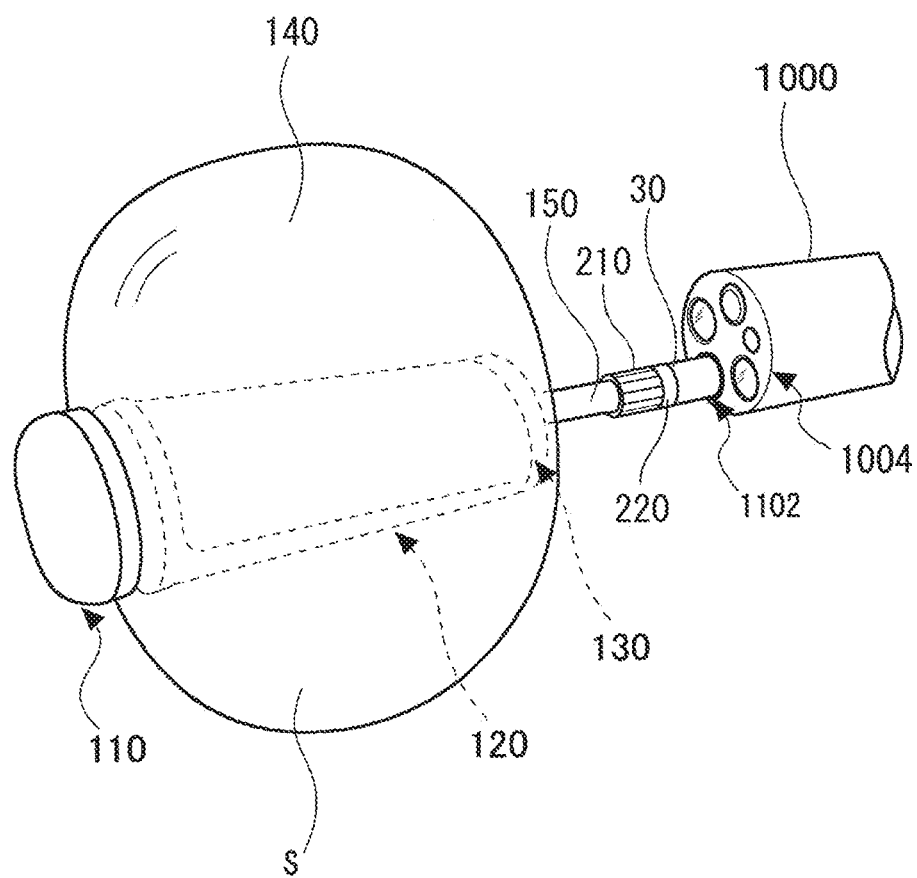
FIG. 13 is a diagram showing an example of the construction of a therapeutic substance conveying device according to an embodiment.

The potential advantage of expanding the balloon 140 by uniform pressure in the circumferential direction of the body portion 100 (FIGS. 13 and 14), as in this embodiment, is as follows. Specifically, by expanding the balloon 140 to fill the biological tract C by continuous supply of air to the balloon 140 (inner space S) even after the therapeutic substance 700 has contacted the affected part AP, it is possible to more satisfactorily press the therapeutic substance 700 against the affected part AP.

Figure 15:
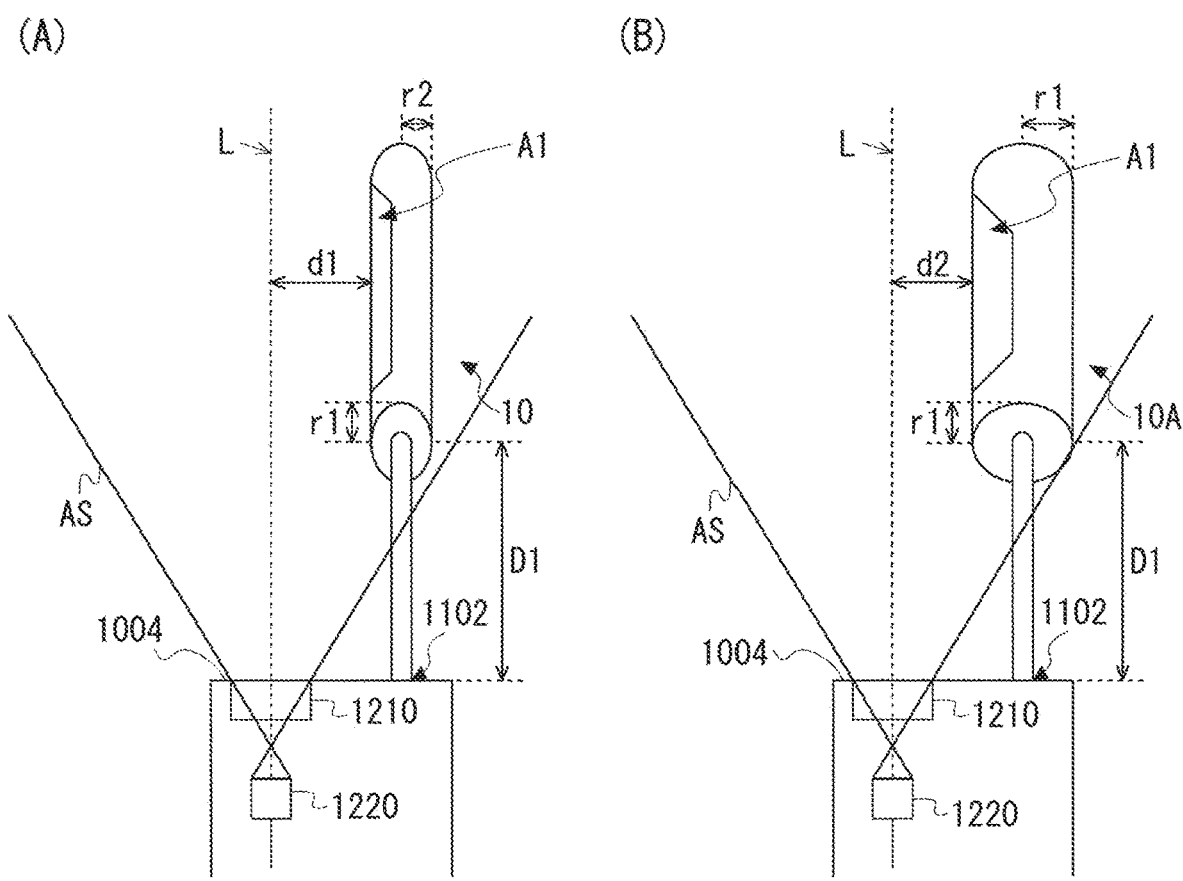
FIG. 15 is a diagram illustrating the reason for forming the main body of the therapeutic substance conveying jig in an elliptical shape.

The reason for forming the body portion 100 in the shape of an ellipse as in this embodiment will now be explained with reference to FIG. 15. FIG. 15(A) schematically shows the range of focusing with the objective lens 1210 (the imaging scope AS of the image sensor) when the therapeutic substance-carrying unit 10 of this embodiment has been moved forward by a distance D1 from the tip of the insertion part 1002. FIG. 15(B) schematically shows the range of focusing with the objective lens 1210 when the therapeutic substance-carrying unit 10A of a comparative example has been moved forward by distance D1 in the same manner as FIG. 15(A).

While the cross-sectional shape of the body portion 100 of the therapeutic substance-carrying unit 10 (the rear edge shape of the other end 130) is an ellipse with r1 as the long radius of (half of the length of the long axis) and r2 as the short radius (half of the length of the short axis) (r1>r2), the cross-sectional shape of the main body of the therapeutic substance-carrying unit 10A (the rear edge shape of the other end) is assumed to be circular with radius r1. When the therapeutic substance-carrying unit 10 and the therapeutic substance-carrying unit 10A are set at an equal distance D1, the distance d1 between the central axis of the objective lens 1210 (the visual axis of the image sensor 1220) L and the recess A1 of the therapeutic substance-carrying unit 10 (FIG. 15(A)) is longer than the distance d2 from the recess A1 of the therapeutic substance-carrying unit 10A. This is because the position of the forceps channel exit hole 1102 of the forceps channel 1100 cannot be changed. The closer the peripheral surface of the main body is to the visual axis L, the less the peripheral surface of the main body will be hidden by the rear edge of the other end. According to this embodiment, therefore, a body portion 100 having a long axis and a short axis is employed and the recess A1 is formed in the short axis direction, the peripheral surface of the body portion 100 (the therapeutic substance 700 held in the recess A1) thereby being included in the image picked up by the image sensor located behind the body portion 100, and therefore the procedural burden of positioning by the doctor can be alleviated.

Modified Example

For this embodiment a balloon 140 is provided to cover the periphery of the middle section 120 of the body portion 100. It is not essential for the balloon 140 to be tubular, and the balloon 140 may simply be attached to the body portion 100 in a manner that blocks at least the recess A, forming an inner space S within the recess A. In this case it would not be necessary to form the through-hole 124.

The one end 110 with an elliptic cylindrical shape was described for this embodiment, and optionally the one end 110 may be formed as an elliptic cylindrical or cylindrical shape with a larger diameter than the middle section 120. In this case, the one end 110 will spread out the biological tract as it proceeds through the biological tract, forming a space between the middle section 120 (recess A) behind it and the inner lumen of the biological tract, so that the therapeutic substance (cell sheet) held in the recess A may be less likely to contact with the biological tract. In this case as well, the tip of the one end 110 is preferably chamfered.

Moreover, for this embodiment, air was used as an example of fluid introduced into the inner space S, but a gas other than air or a liquid (for example, water) may be used instead.

In addition, coloration or marking may be added at the portion of the balloon 140 that is to be drawn into the recess A, to help avoid errors in visual judgment when the therapeutic substance 700 is to be carried before discharge from the inner space S.

Furthermore, for this embodiment, the body portion 100 or body portion 100a is not limited in regard to its coloration, and the body portion 100 or body portion 100a may be transparent or opaque, although the body portion 100 or body portion 100a is preferably opaque for easier visibility of the therapeutic substance being conveyed, and more preferably it has a deep color. Throughout the present specification, "deep color" means black or dark coloration. If the body portion 100 or body portion 100a has a deep color, then when it is used together with an endoscope 1000, less of the light from the phosphor at the tip section of the endoscope 1000 will be reflected, and the therapeutic substance carried on the therapeutic substance-carrying unit 10 or therapeutic substance-carrying unit 10a will be more visible. Here, "dark" means a luminance of less than 50%, and it is not restricted so long as it is a color that exhibits an effect of minimizing reflection of light from the phosphor or rendering the therapeutic substance more visible. There are no particular restrictions on the method of coloration.

2. Therapeutic Substance Conveying Kit

The present invention further relates to a therapeutic substance conveying kit for conveying and/or applying a therapeutic substance to a desired location within a biological tract. According to one embodiment, the therapeutic substance conveying kit of the invention comprises:

a therapeutic substance-carrying unit, a connector to be connected to the therapeutic substance-carrying unit, and an air supply/discharge tube to be connected to the connector, wherein the therapeutic substance-carrying unit has a body portion in which a recess is formed, an elastic membrane covering at least the recess and forming an inner space with the body portion, and a connecting tube of which at least one end is made of a flexible material, and which communicates with the inner space, the connector comprises a coupling body with a through-hole through which fluid passes and having one end for insertion into the connecting tube and the other end connected to the air supply/discharge tube, a flange section anchored to the other end of the coupling body and an anchoring nut through which the coupling body is inserted, the coupling body comprises a tube catch section having a larger diameter than the outer diameter of the coupling body and a smaller diameter than the inner diameter of the anchoring nut, and at least a portion of the inner wall of the anchoring nut is provided with an internal thread, forward screwing of the anchoring nut causes the internal thread to bite into the connecting tube sandwiched between the anchoring nut and the coupling body, and the therapeutic substance-carrying unit is detachable.

With the therapeutic substance conveying kit of the invention, a kit is provided including a therapeutic substance-carrying unit, a connector and an air supply/discharge tube, and the therapeutic substance-carrying unit, connector and air supply/discharge tube in the therapeutic substance conveying kit can be used as requisite components in combination, by a doctor at the place of surgery, for example. Furthermore, when only a certain number of therapeutic substance-carrying units are needed, for example, the therapeutic substance conveying kit of the invention may have the necessary number of therapeutic substance-carrying units provided beforehand, and the therapeutic substance-carrying units alone may be exchanged by the connector.

The therapeutic substance-carrying unit, connector and air supply/discharge tube in the therapeutic substance conveying kit of the invention may be enclosed in a package with either one of each or more than one of each in combination. The therapeutic substance-carrying unit, connector and air supply/discharge tube enclosed in the package is preferably sterilized by optional sterilization means such as gamma sterilization, ultraviolet sterilization, ethylene oxide gas sterilization or hydrogen peroxide gas sterilization, before being enclosed in the package. The sterilization means is not limited so long as it is does not impair the functioning of the constituent elements in the therapeutic substance conveying kit.

According to one embodiment, the therapeutic substance conveying kit of the invention may further comprise inflation means for inflow and discharge of a fluid into the inner space of the therapeutic substance-carrying unit. The inflation means may be, but is not limited to, a syringe, for example. The inflation means may also be packaged with the therapeutic substance-carrying unit, connector and air supply/discharge tube, with either one of each or more than one of each in combination.

According to one embodiment, the therapeutic substance-carrying unit in the therapeutic substance conveying kit of the invention may be a therapeutic substance-carrying unit in which the therapeutic substance is already being carried beforehand. A therapeutic substance-carrying unit in which the therapeutic substance is already being carried may be one that is packaged alone, or packaged together with the connector, air supply/discharge tube and shrinking means, with either one of each or more than one of each in combination, but it is preferably packaged independently alone. A therapeutic substance-carrying unit in which the therapeutic substance is already being carried can simplify the operation of setting the therapeutic substance at the place of surgery, and the surgery time can be shortened.

EXPLANATION OF SYMBOLS

1 Therapeutic substance conveying device
10 Therapeutic substance-carrying unit
10a Therapeutic substance-carrying unit (modified example)
10A Therapeutic substance-carrying unit
20 Connector
30 Air supply/discharge tube
100 Body portion
100a Body portion (modified example)
100b Edge (modified example)
110 One end
112 Groove
120 Middle section
122 Groove
124 Through-hole
130 Other end
132 Open hole
132a Open hole (modified example)
134 Groove
136 Mark
140 Balloon (elastic membrane)
140a Elastic membrane (modified example)
140a' Elastic membrane (modified example)
141 One end
142 Other end
150 Connecting tube
150a Connecting tube (modified example)
151 Internal thread imprint
152 End
200 Coupling body
201 One end
202 Other end
203 Through-hole
204 Tube catch section
204a One end
204b Other end
205 Flow passage hole (part of open hole 132)
210 Anchoring nut
211 Tubular screw part
212 Knurl structure
213 Collar section
214 Insertion hole
215 Internal thread
220 Flange section
230 Nut stopper flange
310 Supply and discharge tube
311 Supply and discharge tube end portion
320 Torque wire 321 End portion
330 Sealing tube material
400 Inflation means
700 Therapeutic substance
700a Therapeutic substance (modified example)
700a' Therapeutic substance (modified example)
1000 Endoscope
1001 Operating unit
1002 Insertion part
1003 Connecting unit
1004 Tip section
1100 Forceps channel
1101 Forceps channel entry hole
1102 Forceps channel exit hole
1103 Curved section
1210 Objective lens
1220 Image sensor
A Recess
A' Recess (modified example)
A1 Recess
AP Affected part
AS Imaging scope of image sensor
C Biological tract
L Visual axis
S Inner space
S1 Inner space
S2 Inner space
S3 Inner space (modified example)

The invention claimed is:

1. A therapeutic substance conveying device for conveying and/or applying a therapeutic substance to a desired site in a biological tract, comprising:
a therapeutic substance-carrying unit,
a connector connected to the therapeutic substance-carrying unit, and
an air supply/discharge tube connected to the connector, wherein
the therapeutic substance-carrying unit has a body portion in which a recess is formed, an elastic membrane covering at least the recess and forming an inner space with the body portion, and a connecting tube of which at least one end is made of a flexible material, and which communicates with the inner space,
the at least one end of the connecting tube does not have an external thread structure,
the connector comprises a coupling body with a through-hole through which fluid passes and having one end for insertion into the connecting tube and the other end connected to the air supply/discharge tube, a flange section anchored to the other end of the coupling body and an anchoring nut through which the coupling body is inserted,
the coupling body comprises a tube catch section having a larger diameter than the outer diameter of the coupling body and a smaller diameter than the inner diameter of the anchoring nut, and
at least a portion of the inner wall of the anchoring nut is provided with an internal thread, forward screwing of the anchoring nut causes the internal thread to bite into the connecting tube sandwiched between the anchoring nut and the coupling body, thereby retaining an internal thread imprint on the connecting tube, and the therapeutic substance-carrying unit is detachable,
wherein the tube catch section lacks an external thread structure,
wherein the air supply/discharge tube is inserted through the forceps channel of an endoscope and is used together with the endoscope, wherein the connector has a smaller diameter than the diameter of the forceps channel.

2. The therapeutic substance conveying device according to claim 1, wherein
the anchoring nut comprises a tubular screw part and a collar section having an insertion hole through which the coupling body is inserted, and
the diameter of the insertion hole is a smaller diameter than the outer diameter of the tube catch section.

3. The therapeutic substance conveying device according to claim 2, wherein the outer diameter of the flange section is a smaller diameter than the outer diameter of the anchoring nut and a larger diameter than the diameter of the insertion hole of the collar section.

4. The therapeutic substance conveying device according to claim 1, wherein the outer diameter of the connector is less than 5.0 mm.

5. The therapeutic substance conveying device according to claim 1, wherein the tube catch section is formed in a tapered manner with increasing diameter from one end of the coupling body toward the other end.

6. The therapeutic substance conveying device according to claim 1, wherein an inflation means for causing inflow and discharge of fluid in the inner space of the therapeutic substance-carrying unit is also connected to the air supply/discharge tube, wherein the inflation means is a syringe or a pump.

7. The therapeutic substance conveying device according to claim 1, wherein the therapeutic substance-carrying unit is for single-use.

8. The therapeutic substance conveying device according to claim 1, wherein the body portion of the therapeutic substance-carrying unit is an approximately half-elliptical tube shape with a portion of the peripheral surface removed.

9. The therapeutic substance conveying device according to claim 1, wherein
the therapeutic substance-carrying unit comprises a body portion having at least a recess-formed middle section between one end and the other end, and
the elastic membrane is formed as a tube with two ends, the one end and the other end of the elastic membrane being in close contact with and anchored to the middle section, while being wrapped around the perimeter of the middle section.

10. The therapeutic substance conveying device according to claim 1, wherein
the body portion of the therapeutic substance-carrying unit has an approximately half-egg shape in which a recess has been formed, and
the elastic membrane is in close contact and anchored with the edge of the body portion.

11. The therapeutic substance conveying device according to claim 1, wherein the body portion has black or dark coloration.

12. A therapeutic substance conveying kit for use of the therapeutic substance conveying device as defined in claim 1, comprising:
a therapeutic substance-carrying unit,
a connector to be connected to the therapeutic substance-carrying unit, and
an air supply/discharge tube to be connected to the connector,
wherein
the therapeutic substance-carrying unit has a body portion in which a recess is formed, an elastic membrane covering at least the recess and forming an inner space with the body portion, and a connecting tube of which at least one end is made of a flexible material, and which communicates with the inner space, the at least one end of the connecting tube does not have an external thread structure, the connector comprises a coupling body with a through-hole through which fluid passes and having one end for insertion into the connecting tube and the other end connected to the air supply/discharge tube, a flange section anchored to the other end of the coupling body and an anchoring nut through which the coupling body is inserted, the coupling body comprises a tube catch section having a larger diameter than the outer diameter of the coupling body and a smaller diameter than the inner diameter of the anchoring nut, and at least a portion of the inner wall of the anchoring nut is provided with an internal thread, forward screwing of the anchoring nut causes the internal thread to bite into the connecting tube sandwiched between the anchoring nut and the coupling body, thereby retaining an internal thread imprint on the connecting tube, and the therapeutic substance-carrying unit is detachable, wherein the tube catch section lacks an external thread structure, wherein the air supply/discharge tube is inserted through the forceps channel of an endoscope and the therapeutic substance conveying device is used together with the endoscope, wherein the connector has a smaller diameter than the diameter of the forceps channel.

13. The therapeutic substance conveying kit according to claim 12, wherein an inflation means for causing inflow and discharge of fluid in the inner space of the therapeutic substance-carrying unit, connected with the air supply/discharge tube, is additionally provided, wherein the inflation means is a syringe or a pump.

14. The therapeutic substance conveying kit according to claim 12, wherein a therapeutic substance is further carried on the therapeutic substance-carrying unit.

15. The therapeutic substance conveying kit according to claim 12, wherein the connecting tube is made from a material suitable for medical use.

16. The therapeutic substance conveying kit according to claim 15, wherein the connecting tube is made from polytetrafluoroethylene (PTFE) or silicone rubber.

17. The therapeutic substance conveying device according to claim 1, wherein the connecting tube is made from a material suitable for medical use.

18. The therapeutic substance conveying device according to claim 17, wherein the connecting tube is made from polytetrafluoroethylene (PTFE) or silicone rubber.

* * * * *